(12) United States Patent
Schuster et al.

(10) Patent No.: US 8,461,178 B2
(45) Date of Patent: Jun. 11, 2013

(54) NAPHTHYRIDINE DERIVATIVES AND THE USE THEREOF AS KINASE INHIBITORS

(75) Inventors: Tilmann Schuster, Grossostheim (DE); Matthias Gerlach, Brachttal (DE); Irene Seipelt, Offenbach (DE); Emmanuel Polymeropoulos, Frankfurt am Main (DE); Gilbert Mueller, Frankfurt am Main (DE); Eckhard Guenther, Maintal (DE); Pascal Marchand, Nort-sur-Erdre (FR); Julien Defaux, Dijon (FR)

(73) Assignee: Aeterna Zentaris GmbH, Frankfurt (DE)

( * ) Notice: Subject to any disclaimer, the term of this patent is extended or adjusted under 35 U.S.C. 154(b) by 321 days.

(21) Appl. No.: 12/953,680

(22) Filed: Nov. 24, 2010

(65) Prior Publication Data

US 2011/0150831 A1 Jun. 23, 2011

Related U.S. Application Data

(60) Provisional application No. 61/264,711, filed on Nov. 27, 2009.

(30) Foreign Application Priority Data

Nov. 26, 2009 (EP) .................................... 09177132

(51) Int. Cl.
*A61K 31/44* (2006.01)
*C07D 471/02* (2006.01)

(52) U.S. Cl.
USPC ............................................ 514/300; 546/122

(58) Field of Classification Search
USPC ........................................... 546/122; 514/300
See application file for complete search history.

(56) References Cited

U.S. PATENT DOCUMENTS 6,822,097 B1   11/2004   Norman et al.
7,405,299 B2 *  7/2008   Beight et al. .................. 544/353
2007/0032518 A1  2/2007   Norman et al.

FOREIGN PATENT DOCUMENTS

WO  WO 03/066630 A2   8/2003
WO  WO 2009/093049 A1  7/2009
WO  WO 2009/130317 A1  10/2009

OTHER PUBLICATIONS

International Search Report issued Feb. 8, 2011 in Application No. PCT/EP2010/068119.

* cited by examiner

*Primary Examiner* — Niloofar Rahmani
(74) *Attorney, Agent, or Firm* — Oblon, Spivak, McClelland, Maier & Neustadt, L.L.P.

(57) ABSTRACT

The present invention relates to kinase modulators of the naphthyridine type and to the preparation and use thereof as medicaments for the modulation of misdirected cellular signal transduction processes, in particular for influencing the function of tyrosine and serine/threonine kinases and for the treatment of malignant or benign tumors and other disorders based on pathological cell proliferation, such as, for example, restenosis, psoriasis, arteriosclerosis and cirrhosis of the liver.

9 Claims, No Drawings

NAPHTHYRIDINE DERIVATIVES AND THE USE THEREOF AS KINASE INHIBITORS

TECHNICAL FIELD

The present invention relates to kinase modulators of the naphthyridine type and to the preparation and use thereof as medicaments for the modulation of misdirected cellular signal transduction processes, in particular for influencing the function of tyrosine and serine/threonine kinases and for the treatment of malignant or benign tumours and other disorders based on pathological cell proliferation, such as, for example, restenosis, psoriasis, arteriosclerosis and cirrhosis of the liver.

STATE OF THE ART

Activation of protein kinases is a central event in cellular signal transduction processes. Aberrant kinase activation is observed in various pathological states. Targeted inhibition of kinases is therefore a fundamental therapeutic aim.

The phosphorylation of proteins is generally initiated by extracellular signals and represents a universal mechanism for controlling various cellular events such as, for example, metabolic processes, cell growth, cell migration, cell differentiation, membrane transport and apoptosis. The kinase protein family is responsible for protein phosphorylation. These enzymes catalyse transfer of phosphate to specific substrate proteins. Based on the substrate specificity, the kinases are divided into two main classes, the tyrosine kinases and the serine/threonine kinases. Both the receptor tyrosine kinases and the cytoplasmic tyrosine and serine/threonine kinases are important proteins in cellular signal transduction. Overexpression or degradation of these proteins plays an important part in disorders based on pathological cell proliferations. These include inter alia metabolic disorders, disorders of the connective tissue and of the blood vessels, and malignant and benign tumours. In tumour initiation and development they frequently occur as oncogens, i.e. as aberrant, constitutively active kinase proteins. The consequences of this excessive kinase activation are, for example, uncontrolled cell growth and reduced cell death. Stimulation of tumour-induced growth factors may also be the cause of overstimulation of kinases. Development of kinase modulators is therefore of particular interest for all pathogenic processes influenced by kinases.

The invention is therefore directed at generating novel compounds which are suitable as modulators of receptor tyrosine kinases and cytoplasmic tyrosine and serine/threonine kinases. Since not all kinases connected one behind the other in misdirected signal transduction cascades—such as, for example, in the case of Raf/Mek/Erk—have to be present as oncogenic kinases or as constitutively active enzymes, in this invention the non-active kinases will also be considered to be therapeutic target proteins, i.e. the new compounds can bind both to active and also to non-active kinases and therefore influence the signal transduction.

Naphythyridine derivatives are finding many applications in pharmaceutical industry as pharmacodynamically active compounds and as building blocks for syntheses.

Naphthyridine derivatives are described in the document BMCL 2009, 19, 3568 as MCH1R inhibitors, in the patent WO2008/153752 as modulators of fatty acid amide hydrolase and in the patents DE 2650826, WO 00/21952, WO 00/43383, WO 01/07432, WO 02/056882, WO 02/08224 and WO2006/021448 as antibacterial agents. In the patents WO 99/58533, US 2007/0160538 and in the literature reference BMCL 2001, 11, 1907 naphthyridines are described as orexin-1 receptor antagonists. Substituted naphthyridines are described in the patent WO2000066583 as tyrosine kinase inhibitors and in the patent application WO2008150827 as PI3 kinase inhibitors.

DESCRIPTION OF THE INVENTION

The present invention relates to kinase modulators of the naphthyridine type and to the preparation and use thereof as medicaments for the modulation of misdirected cellular signal transduction processes, in particular for influencing the function of tyrosine and serine/threonine kinases and for the treatment of malignant or benign tumours and other disorders based on pathological cell proliferation, such as, for example, restenosis, psoriasis, arteriosclerosis and cirrhosis of the liver.

It has now been found, surprisingly, that novel compounds from the naphthyridine series which are substituted in position 2, 3 or 4 for example by urea, thiourea, guanidine or amidine groups are suitable for producing medicaments for the modulation of misdirected cellular signal transduction processes, in particular for influencing the function of tyrosine and serine/threonine kinases and for the treatment of malignant or benign tumours, such as, e.g. of the breast, prostate, lung, colon, skin and ovaries and other disorders based on pathological cell proliferations. According to this aspect, the present application describes novel compounds from the naphthyridine series of the general Formula I

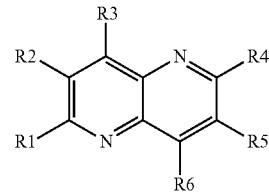

Formula I in which the substituents R1-R6 have the following meaning:
R1, R2 and R3 can, independently of each other, be
(i) hydrogen,
(ii) unsubstituted or substituted alkyl,
(iii) unsubstituted or substituted heterocyclyl,
(iv) unsubstituted or substituted aryl,
(v) unsubstituted or substituted heteroaryl,
(vi) halogen,
(vii) cyano,
(viii) hydroxyl,
(ix) alkoxy,
(x) amino,
(xi) carboxyl, alkoxycarbonyl, carboxyalkyl or alkoxycarbonylalkyl,
(xii) alkoxycarbonylamino, alkoxycarbonylaminoalkyl, and
(xiii) NR7R8
where at least one of the substituents R1-R3 has to be an NR7R8 and
where R7 can be hydrogen, alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl substituents can, for their part, in turn be substituted,
and R8 may be:
—C(Y)NR9R10, where Y is O, S and R9 and R10 may be independently of one another
(i) hydrogen,
(ii) unsubstituted or substituted alkyl,
(iii) unsubstituted or substituted cycloalkyl, (iv) unsubstituted or substituted heterocyclyl,
(v) unsubstituted or substituted aryl,
(vi) unsubstituted or substituted heteroaryl,
(vii) or R9 and R10 together may be heterocyclyl,
—C(Y)NR11R12, where Y is NH and R11 and R12 may be independently of one another
(i) hydrogen,
(ii) unsubstituted or substituted alkyl,
(iii) unsubstituted or substituted cycloalkyl,
(iv) unsubstituted or substituted heterocyclyl,
(v) unsubstituted or substituted aryl,
(vi) unsubstituted or substituted heteroaryl,
(vii) or R11 and R12 together may be heterocyclyl,
—C(NR13)R14 where R13 is H and R14 may be
(i) unsubstituted or substituted alkyl,
(ii) unsubstituted or substituted cycloalkyl,
(iii) unsubstituted or substituted heterocyclyl,
(iv) unsubstituted or substituted aryl,
(v) unsubstituted or substituted heteroaryl,
R4, R5 and R6 may be independently of one another:
(i) hydrogen,
(ii) unsubstituted or substituted alkyl,
(iii) unsubstituted or substituted cycloalkyl,
(iv) unsubstituted or substituted heterocyclyl,
(v) unsubstituted or substituted aryl,
(vi) unsubstituted or substituted heteroaryl,
(vii) halogen,
(viii) cyano,
(ix) hydroxyl,
(x) alkoxy,
(xi) NR15R16, where R15 and R16 can, independently of each other, be hydrogen, alkyl, cycloalkyl, heterocyclyl, aryl, heteroaryl, alkylcyclyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl substituents can, for their part, in turn be substituted,
or R15 and R16 are together heterocyclyl, where heterocyclyl can, for their part, in turn be substituted,
(xii) OR17, where R17 can be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl, heteroaryl, alkylcycloalkyl, alkylheterocyclyl, alkylaryl or alkylheteroaryl substituents can, for their part, in turn be substituted,
(xiii) SR18, where R18 can be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl substituents can, for their part, in turn be substituted,
where at least one of the substituents R4-R6 has to be an unsubstituted or substituted (hetero)aryl or NR15R16.

The term "halogen" for the purposes of this invention refers to one, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom.

The term "alkyl" includes for the purpose of this invention acyclic saturated or unsaturated hydrocarbon radicals which may be branched or straight-chain and unsubstituted or mono- or polysubstituted, having 1 to 12 C atoms, i.e. $C_{1-12}$-alkanyls, $C_{2-12}$-alkenyls and $C_{2-12}$-alkynyls. In this connection, alkenyls have at least one C—C double bond and alkynyls have at least one C—C triple bond. Alkyl is preferably selected from the group comprising methyl, ethyl, n-propyl, 2-propyl, n-butyl, sec-butyl, tert-butyl, n-pentyl, isopentyl, neopentyl, n-hexyl, 2-hexyl, n-octyl, n-nonyl, n-decyl, n-undecyl, n-dodecyl, ethylenyl (vinyl), ethynyl, propenyl (—CH$_2$CH=CH$_2$; —CH=CH—CH$_3$, —C(=CH$_2$)—CH$_3$), propynyl (—CH$_2$—C≡CH, —C≡C—CH$_3$), butenyl, butynyl, pentenyl, pentynyl, hexenyl, hexynyl, heptenyl, heptynyl, octenyl, and octynyl.

By the term "alkoxy" as used herein is meant —O(alkyl) including —OCH3, —OCH2CH3 and —OC(CH3)3 where alkyl is as described herein.

The term "cycloalkyl" means for the purposes of this invention cyclic hydrocarbon radicals having 3-12 carbon atoms, which may be saturated or unsaturated. It is possible for the linkage to the compounds of the general structure I to take place via any possible ring member of the cycloalkyl radical. The cycloalkyl radical may also be part of a bi- or polycyclic system.

The term "heterocyclyl" stands for a 3-, 4-, 5-, 6-, 7- or 8-membered cyclic organic radical which comprises at least 1, where appropriate 2, 3, 4 or 5, heteroatoms, the heteroatoms being identical or different and the cyclic radical being saturated or unsaturated, but not aromatic. It is possible for the linkage to the compounds of the general structure I to take place via any possible ring member of the heterocyclyl radical. The heterocycle may also be part of a bi- or polycyclic system. Preferred heteroatoms are nitrogen, oxygen and sulphur. It is preferred for the heterocyclyl radical to be selected from the group comprising tetrahydrofuryl, tetrahydropyranyl, pyrrolidinyl, piperidinyl, piperazinyl and morpholinyl.

The term "aryl" means for the purpose of this invention aromatic hydrocarbons having 6 to 14 carbon atoms, inter alia phenyls, naphthyls and anthracenyls. The radicals may also be fused to other saturated, (partially) unsaturated or aromatic ring systems. It is possible for the linkage to the compounds of the general structure I to take place via any possible ring member of the aryl radical.

The term "heteroaryl" stands for a 5-, 6- or 7-membered cyclic aromatic radical which comprises at least 1, where appropriate also 2, 3, 4 or 5, heteroatoms, the heteroatoms being identical or different. It is possible for the linkage to the compounds of the general structure I to take place via any possible ring member of the heteroaryl radical. The heterocycle may also be part of a bi- or polycyclic system. Preferred heteroatoms are nitrogen, oxygen and sulphur. It is preferred for the heteroaryl radical to be selected from the group comprising pyrrolyl, furyl, thienyl, thiazolyl, oxazolyl, oxadiazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl, acridinyl.

The terms "alkyl-cycloalkyl", "alkyl-heterocyclyl", "alkyl-aryl" or "alkyl-heteroaryl" means for the purposes of the present invention that alkyl and cycloalkyl, heterocyclyl, aryl and heteroaryl have the meanings defined above, and the cycloalkyl, heterocyclyl, aryl or heteroaryl radical is linked via a $C_{1-8}$-alkyl group to the compounds of the general structure I.

The term substituted in connection with "alkyl", "cycloalkyl", "heterocyclyl", "aryl", "heteroaryl", "alkyl-cycloalkyl", "alkyl-heterocyclyl", "alkyl-aryl", and "alkyl-heteroaryl" means for the purposes of this invention, unless explicitly defined above in the description or the claims, replacement of one or more hydrogen radicals by F, Cl, Br, I, $CF_3$, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O-(CH$_2$)$_n$—O, OC(O)-alkyl, OC(O)-cycloalkyl, OC(O)-heterocyclyl, OC(O)-aryl, OC(O)-heteroaryl, OSO$_2$-alkyl OSO$_2$-cycloalkyl, OSO$_2$-aryl, OSO$_2$-heteroaryl, O—P(O)(OH)$_2$, O—P(O)(O-alkyl)$_2$, alkyl-P(O)(OH)$_2$, alkyl-P(O)(O-alkyl)$_2$, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_3$H, SO$_2$O-alkyl, SO$_2$O-aryl, SO$_2$O-heteroaryl, alkyl, cycloalkyl, heterocyclyl, aryl or heteroaryl substituents, and n may have the value 1, 2 or 3, and the alkyl, cycloalkyl, heterocyclyl, aryl and heteroaryl substituents may in turn themselves be substituted.

The substituents may be identical or different, and the substitution may take place at any possible position of the alkyl, cycloalkyl, heterocyclyl, aryl and heteroaryl radical.

Radicals substituted more than once mean those which are substituted more than once, e.g. twice or three times, either on different or on the same atoms, for example three times on the same C atom as in the case of CF$_3$, —CH$_2$CF$_3$, or in different sites as in the case of —CH(OH)—CH═CH—CHCl$_2$. Substitution more than once can take place with identical or different substituents.

Where the compounds of the invention of the general Formula I have at least one centre of asymmetry, they may exist in the form of their racemates, in the form of the pure enantiomers and/or diastereomers or in the form of mixtures of these enantiomers and/or diastereomers. Any mixing ratio of the stereoisomers in the mixtures is possible. Thus, for example, the compounds of the invention of the general Formula I which have one or more centres of chirality and which occur as racemates can be separated by methods known per se into their optical isomers, i.e. enantiomers or diastereomers. The separation can take place by column separation on chiral phases or by recrystallization from an optically active solvent or with use of an optically active acid or base or through derivatization with an optically active reagent such as, for example, an optically active alcohol, and subsequent elimination of the radical.

Where possible, the compounds of the invention may exist in the form of tautomers.

The compounds of the invention of the general Formula I may, if they contain a sufficiently basic group such as, for example, a primary, secondary or tertiary amine, be converted with inorganic and organic acids into their physiologically tolerated salts. The pharmaceutically acceptable salts of the compounds of the invention of the general structure I are preferably formed with hydrochloric acid, hydrobromic acid, sulphuric acid, phosphoric acid, methanesulphonic acid, p-toluenesulphonic acid, carbonic acid, formic acid, acetic acid, trifluoroacetic acid, sulphoacetic acid, oxalic acid, malonic acid, maleic acid, succinic acid, tartaric acid, racemic acid, malic acid, embonic acid, mandelic acid, fumaric acid, lactic acid, citric acid, glutamic acid or aspartic acid. The salts which are formed are, inter alia, hydrochlorides, hydrobromides, sulphates, bisulphates, phosphates, methanesulphonates, tosylates, carbonates, bicarbonates, formates, acetates, triflates, sulphoacetates, oxalates, malonates, maleates, succinates, tartrates, malates, embonates, mandelates, fumarates, lactates, citrates, glutamates and aspartates. The stoichiometry of the salts which are formed of the compounds of the invention may moreover be integral or nonintegral multiples of one.

The compounds of the invention of the general Formula I may, if they contain a sufficiently acidic group such as a carboxyl group, be converted with inorganic and organic bases into their physiologically tolerated salts. Examples of suitable inorganic bases are sodium hydroxide, potassium hydroxide, calcium hydroxide, and of organic bases are ethanolamine, diethanolamine, triethanolamine, cyclohexylamine, dibenzylethylenediamine and lysine. The stoichiometry of the salts which are formed of the compounds of the invention may moreover be integral or nonintegral multiples of one.

Preference is likewise given to solvates and, in particular, hydrates of the compounds of the invention which can be obtained for example by crystallization from a solvent or from aqueous solution. It is possible in these cases for one, two, three or any number of solvate or water molecules to combine with the compounds of the invention to give solvates and hydrates.

It is known that chemical substances form solids in various order states which are referred to as polymorphic forms or modifications. The various modifications of a polymorphic substance may vary widely in their physical properties. The compounds of the invention of the general Formula I can exist in various polymorphic forms, and certain modifications may be metastable.

Most preference is given to compounds of the general formula I which are chosen from the following selection:
1-Ethyl-3-[7-(4-methoxy-phenyl)-[1,5]naphthyridin-2-yl]-urea (1)
1-[7-(3,4-Dimethoxy-phenyl)-[1,5]naphthyridin-2-yl]-3-ethyl-urea (2)
1-tert-Butyl-3-[7-(3,4-dimethoxy-phenyl)-[1,5]naphthyridin-2-yl]-urea (3)
1-tert-Butyl-3-[7-(4-hydroxy-3-methoxy-phenyl)-[1,5]naphthyridin-2-yl]-urea (4)
1-[7-(1-Methyl-1H-pyrazol-4-yl)-[1,5]naphthyridin-2-yl]-3-phenethyl-urea (5)
1-Ethyl-3-[7-(3,4,5-trimethoxy-phenylamino)-[1,5]naphthyridin-2-yl]-thiourea (6)
1-[7-(3,4-Dimethoxy-phenyl)-[1,5]naphthyridin-4-yl]-3-ethyl-urea (7)
1-tert-Butyl-3-[7-(3,4-dimethoxy-phenyl)-[1,5]naphthyridin-4-yl]-urea (8)
1-Ethyl-3-[7-(4-hydroxy-3-methoxy-phenyl)-[1,5]naphthyridin-4-yl]-urea (9)
1-Ethyl-3-[7-(1-methyl-1H-pyrazol-4-yl)-[1,5]naphthyridin-4-yl]-urea (10)
1-tert-Butyl-3-[7-(1-methyl-1H-pyrazol-4-yl)-[1,5]naphthyridin-4-yl]-urea (11)
1-tert-Butyl-3-[7-(4-hydroxy-3-methoxy-phenyl)-[1,5]naphthyridin-4-yl]-urea (12)
1-tert-Butyl-3-[7-(3,5-dichloro-4-hydroxy-phenyl)-[1,5]naphthyridin-4-yl]-urea (13)
1-Cyclopropyl-3-[7-(4-hydroxy-3-methoxy-phenyl)-[1,5]naphthyridin-4-yl]-urea (14)

1-[7-(3,5-Dichloro-4-hydroxy-phenyl)-[1,5]naphthyridin-4-yl]-3-ethyl-urea (15)

1-Ethyl-3-[7-(4-hydroxy-3,5-dimethyl-phenyl)-[1,5]naphthyridin-4-yl]-urea (16)

1-Cyclobutyl-3-[7-(1-methyl-1H-pyrazol-4-yl)-[1,5]naphthyridin-4-yl]-urea (17)

1-Cyclopropyl-3-[7-(1-methyl-1H-pyrazol-4-yl)-[1,5]naphthyridin-4-yl]-urea (18)

1-[7-(1-Methyl-1H-pyrazol-4-yl)-[1,5]naphthyridin-4-yl]-3-propyl-urea (19)

1-[7-(1-Methyl-1H-pyrazol-4-yl)-[1,5]naphthyridin-4-yl]-3-(2,2,2-trifluoro-ethyl)-urea (20)

1-[7-(1-Methyl-1H-pyrazol-4-yl)-[1,5]naphthyridin-4-yl]-3-(4-phenyl-butyl)-urea (21)

1-Cyclohexyl-3-[7-(1-methyl-1H-pyrazol-4-yl)-[1,5]naphthyridin-4-yl]-urea (22)

1-[7-(1-Methyl-1H-pyrazol-4-yl)-[1,5]naphthyridin-4-yl]-3-phenyl-urea (23)

1-(3,3-Difluoro-cyclobutyl)-3-[7-(1-methyl-1H-pyrazol-4-yl)-[1,5]naphthyridin-4-yl]-urea (24)

1-Hexyl-3-[7-(1-methyl-1H-pyrazol-4-yl)-[1,5]naphthyridin-4-yl]-urea (25)

1-tert-Butyl-3-[7-(1-methyl-1H-pyrazol-4-yl)-[1,5]naphthyridin-2-yl]-urea (26)

1-[7-(1-Methyl-1H-pyrazol-4-yl)-[1,5]naphthyridin-2-yl]-3-phenyl-urea (27)

1-Benzyl-3-[7-(1-methyl-1H-pyrazol-4-yl)-[1,5]naphthyridin-2-yl]-urea (28)

1-[7-(1-Methyl-1H-pyrazol-4-yl)-[1,5]naphthyridin-2-yl]-3-(4-phenyl-butyl)-urea (29)

1-Isopropyl-3-[7-(1-methyl-1H-pyrazol-4-yl)-[1,5]naphthyridin-4-yl]-urea (30)

1-Benzyl-3-[7-(1-methyl-1H-pyrazol-4-yl)-[1,5]naphthyridin-4-yl]-urea (31)

1-Butyl-3-[7-(1-methyl-1H-pyrazol-4-yl)-[1,5]naphthyridin-4-yl]-urea (32)

1-[7-(1-Methyl-1H-pyrazol-4-yl)-[1,5]naphthyridin-4-yl]-3-phenethyl-urea (33)

1-Cyclopentyl-3-[7-(1-methyl-1H-pyrazol-4-yl)-[1,5]naphthyridin-4-yl]-urea (34)

1-Cyclopropyl-3-[7-(1H-pyrazol-4-yl)-[1,5]naphthyridin-4-yl]-urea (35)

1-Cyclopropyl-3-(7-thiophen-3-yl-[1,5]naphthyridin-4-yl)-urea (36)

1-Cyclopropyl-3-[7-(2-fluoro-pyridin-4-yl)-[1,5]naphthyridin-4-yl]-urea (37)

1-Cyclopropyl-3-{7-[1-(2-morpholin-4-yl-ethyl)-1H-pyrazol-4-yl]-[1,5]naphthyridin-4-yl}-urea (38)

1-Cyclopropyl-3-(7-phenyl-[1,5]naphthyridin-4-yl)-urea (39)

1-Cyclopropyl-3-[7-(1H-indol-5-yl)-[1,5]naphthyridin-4-yl]-urea (40)

The naphthyridines of the general formula I according to the invention are suitable for use in medicaments, in particular as agents for the treatment of disorders which result from misdirected cellular signal transduction processes in humans, mammals and poultry. Mammals may be domesticated animals such as horses, cattle, dogs, cats, hares, sheep and the like.

According to a further aspect of the invention there is provided a method for treating disorders which result from misdirected cellular signal transduction processes in humans and other mammals, characterized in that at least one naphthyridine according to the general formula I is administered to the human or another mammal in a dose effective for the treatment of these disorders. The therapeutically effective dose, to be administered for the treatment, of the respective naphthyridine according to the invention depends inter alia on the type and the stage of the disorder, on the age, weight and sex of the patient, on the type of administration and on the duration of the treatment. The medicaments according to the invention can be administered as liquid, semisolid and solid pharmaceutical forms. This takes place in the manner suitable in each case in the form of aerosols, powders, dusting powders and epipastics, tablets including coated tablets, emulsions, foams, solutions, suspensions, gels, ointments, pastes, pills, pastilles, capsules or suppositories.

The pharmaceutical forms comprise besides at least one ingredient of the invention, depending on the pharmaceutical form employed, where appropriate auxiliaries such as, inter alia, solvents, solution promoters, solubilizers, emulsifiers, wetting agents, antifoams, gelling agents, thickeners, film formers, binders, buffers, salt formers, desiccants, flow regulators, fillers, preservatives, antioxidants, colours, mould release agents, lubricants, disintegrants, and masking tastes and odours. The selection of the auxiliaries, and the amounts thereof to be employed, depends on the chosen pharmaceutical form and is based on the formulas known to the skilled person.

The medicaments according to the invention can be administered in a suitable dosage form to the skin, epicutaneously as solution, suspension, emulsion, foam, ointment, paste or plaster; via the oral and lingual mucosa, buccally, lingually or sublingually as tablet, pastille, coated tablet, linctus or gargle; via the gastric and intestinal mucosa, enterally as tablet, coated tablet, capsule, solution, suspension or emulsion; via the rectal mucosa, rectally as suppository, rectal capsule or ointment; via the nasal mucosa, nasally as drops, ointments or spray; via the bronchial and alveolar epithelium, by the pulmonary route or by inhalation as aerosol or inhalant; via the conjunctiva, conjunctivally as eyedrops, eye ointment, eye tablets, lamellae or eye lotion; via the mucosa of the genital organs, intravaginally as vaginal suppositories, ointments and douche, by the intrauterine route as uterine pessary; via the urinary tract, intraurethrally as irrigation, ointment or bougie; into an artery, intraarterially as injection; into a vein, intravenously as injection or infusion, paravenously as injection or infusion; into the skin, intracutaneously as injection or implant; under the skin, subcutaneously as injection or implant; into the muscle, intramuscularly as injection or implant; into the abdominal cavity, intraperitoneally as injection or infusion.

The medicinal effect of the compounds of the invention of the general structure I can be prolonged by suitable measures in the light of practical therapeutic requirements. This aim can be achieved by chemical and/or pharmaceutical means. Examples of the achievement of a prolongation of the effect are the use of implants, liposomes, delayed-release forms, nanoparticle suspensions and so-called prodrugs of the compounds according to the invention, the formation of salts and complexes of low solubility, or the use of crystal suspensions.

The compounds according to the invention can be employed as individual substances or in combination with other substances such as, for example, asparaginase, bleomycin, carboplatin, carmustine, chlorambucil, cisplatin, colaspase, cyclophosphamide, cytarabine, dacarbazine, dactinomycin, daunorubicin, doxorubicin (adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thalidomide, thioguanine, topotecan, vinblastine, vincristine, vindesine, aminoglutethimide, L-asparaginase, azathioprine, 5-azacytidine cladribine, busulphan, diethylstilbestrol, 2',2'-difluorodeoxycytidine, docetaxel, erythrohydroxynonyladenine, ethynylestradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbine, epothilone, gemcitabine, taxotere, BCNU, CCNU, DTIC, herceptin, avastin, erbitux, sorafenib (nexavar), imatinib (gleevec, glivec), gefitinib (iressa), erlotinib (tarceva), rapamycin, actinomycin D, sunitinib (sutent), dasatinib (sprycel), nilotinib (tasigna), lapatinib (tykerb, tyverb), vatalanib.

Particular preference is given here to medicaments comprising at least one compound of the following group of naphthyridines:

1-Ethyl-3-[7-(4-methoxy-phenyl)-[1,5]naphthyridin-2-yl]-urea (1)
1-[7-(3,4-Dimethoxy-phenyl)-[1,5]naphthyridin-2-yl]-3-ethyl-urea (2)
1-tert-Butyl-3-[7-(3,4-dimethoxy-phenyl)-[1,5]naphthyridin-2-yl]-urea (3)
1-tert-Butyl-3-[7-(4-hydroxy-3-methoxy-phenyl)-[1,5]naphthyridin-2-yl]-urea (4)
1-[7-(1-Methyl-1H-pyrazol-4-yl)-[1,5]naphthyridin-2-yl]-3-phenethyl-urea (5)
1-Ethyl-3-[7-(3,4,5-trimethoxy-phenylamino)-[1,5]naphthyridin-2-yl]-thiourea (6)
1-[7-(3,4-Dimethoxy-phenyl)-[1,5]naphthyridin-4-yl]-3-ethyl-urea (7)
1-tert-Butyl-3-[7-(3,4-dimethoxy-phenyl)-[1,5]naphthyridin-4-yl]-urea (8)
1-Ethyl-3-[7-(4-hydroxy-3-methoxy-phenyl)-[1,5]naphthyridin-4-yl]-urea (9)
1-Ethyl-3-[7-(1-methyl-1H-pyrazol-4-yl)-[1,5]naphthyridin-4-yl]-urea (10)
1-tert-Butyl-3-[7-(1-methyl-1H-pyrazol-4-yl)-[1,5]naphthyridin-4-yl]-urea (11)
1-tert-Butyl-3-[7-(4-hydroxy-3-methoxy-phenyl)-[1,5]naphthyridin-4-yl]-urea (12)
1-tert-Butyl-3-[7-(3,5-dichloro-4-hydroxy-phenyl)-[1,5]naphthyridin-4-yl]-urea (13)
1-Cyclopropyl-3-[7-(4-hydroxy-3-methoxy-phenyl)-[1,5]naphthyridin-4-yl]-urea (14)
1-[7-(3,5-Dichloro-4-hydroxy-phenyl)-[1,5]naphthyridin-4-yl]-3-ethyl-urea (15)
1-Ethyl-3-[7-(4-hydroxy-3,5-dimethyl-phenyl)-[1,5]naphthyridin-4-yl]-urea (16)
1-Cyclobutyl-3-[7-(1-methyl-1H-pyrazol-4-yl)-[1,5]naphthyridin-4-yl]-urea (17)
1-Cyclopropyl-3-[7-(1-methyl-1H-pyrazol-4-yl)-[1,5]naphthyridin-4-yl]-urea (18)
1-[7-(1-Methyl-1H-pyrazol-4-yl)-[1,5]naphthyridin-4-yl]-3-propyl-urea (19)
1-[7-(1-Methyl-1H-pyrazol-4-yl)-[1,5]naphthyridin-4-yl]-3-(2,2,2-trifluoro-ethyl)-urea (20)
1-[7-(1-Methyl-1H-pyrazol-4-yl)-[1,5]naphthyridin-4-yl]-3-(4-phenyl-butyl)-urea (21)
1-Cyclohexyl-3-[7-(1-methyl-1H-pyrazol-4-yl)-[1,5]naphthyridin-4-yl]-urea (22)
1-[7-(1-Methyl-1H-pyrazol-4-yl)-[1,5]naphthyridin-4-yl]-3-phenyl-urea (23)
1-(3,3-Difluoro-cyclobutyl)-3-[7-(1-methyl-1H-pyrazol-4-yl)-[1,5]naphthyridin-4-yl]-urea (24)
1-Hexyl-3-[7-(1-methyl-1H-pyrazol-4-yl)-[1,5]naphthyridin-4-yl]-urea (25)
1-tert-Butyl-3-[7-(1-methyl-1H-pyrazol-4-yl)-[1,5]naphthyridin-2-yl]-urea (26)
1-[7-(1-Methyl-1H-pyrazol-4-yl)-[1,5]naphthyridin-2-yl]-3-phenyl-urea (27)
1-Benzyl-3-[7-(1-methyl-1H-pyrazol-4-yl)-[1,5]naphthyridin-2-yl]-urea (28)
1-[7-(1-Methyl-1H-pyrazol-4-yl)-[1,5]naphthyridin-2-yl]-3-(4-phenyl-butyl)-urea (29)
1-Isopropyl-3-[7-(1-methyl-1H-pyrazol-4-yl)-[1,5]naphthyridin-4-yl]-urea (30)
1-Benzyl-3-[7-(1-methyl-1H-pyrazol-4-yl)-[1,5]naphthyridin-4-yl]-urea (31)
1-Butyl-3-[7-(1-methyl-1H-pyrazol-4-yl)-[1,5]naphthyridin-4-yl]urea (32)
1-[7-(1-Methyl-1H-pyrazol-4-yl)-[1,5]naphthyridin-4-yl]-3-phenethyl-urea (33)
1-Cyclopentyl-3-[7-(1-methyl-1H-pyrazol-4-yl)-[1,5]naphthyridin-4-yl]-urea (34)
1-Cyclopropyl-3-[7-(1H-pyrazol-4-yl)-[1,5]naphthyridin-4-yl]-urea (35)
1-Cyclopropyl-3-(7-thiophen-3-yl-[1,5]naphthyridin-4-yl)-urea (36)
1-Cyclopropyl-3-[7-(2-fluoro-pyridin-4-yl)-[1,5]naphthyridin-4-yl]-urea (37)
1-Cyclopropyl-3-{7-[1-(2-morpholin-4-yl-ethyl)-1H-pyrazol-4-yl]-[1,5]naphthyridin-4-yl}-urea (38)
1-Cyclopropyl-3-(7-phenyl-[1,5]naphthyridin-4-yl)-urea (39)
1-Cyclopropyl-3-[7-(1H-indol-5-yl)-[1,5]naphthyridin-4-yl]-urea (40)

These compounds can be present as the free base or else as salts of physiologically acceptable acids.

Chemical Synthesis

The compounds of the general formula I can be obtained according to Schemes 1-4 below:

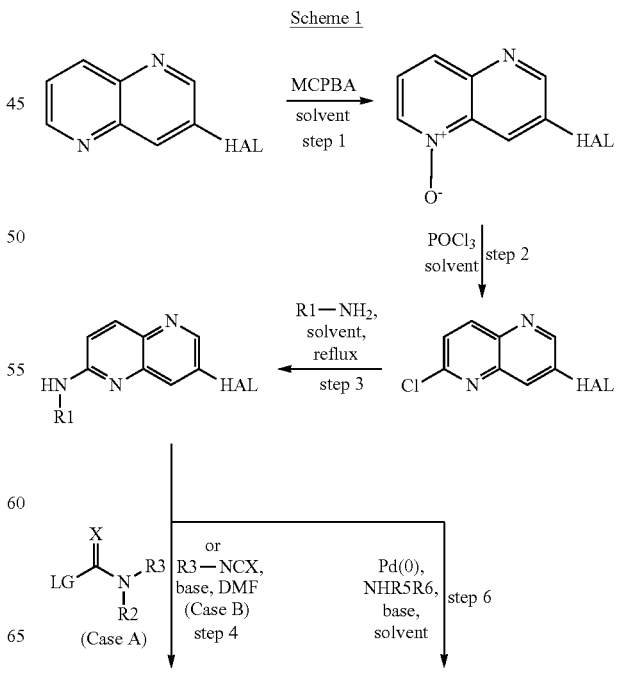

Scheme 1

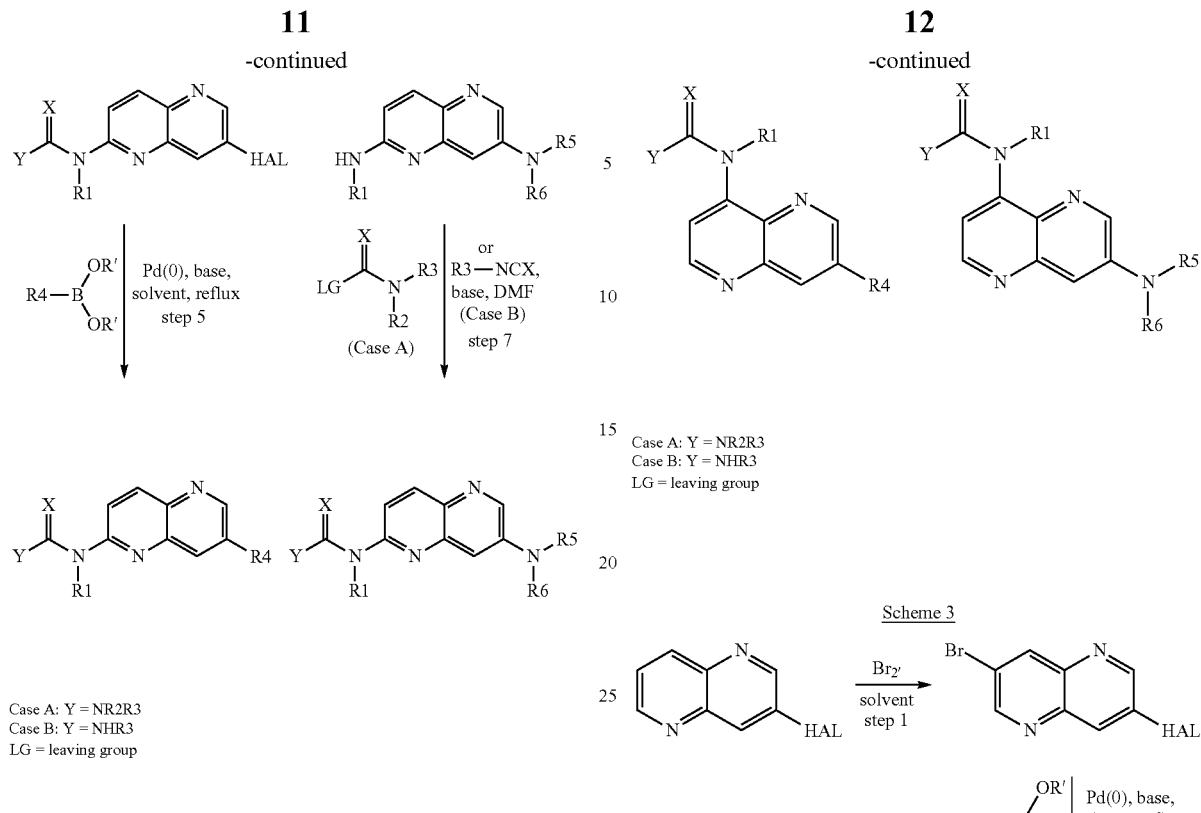
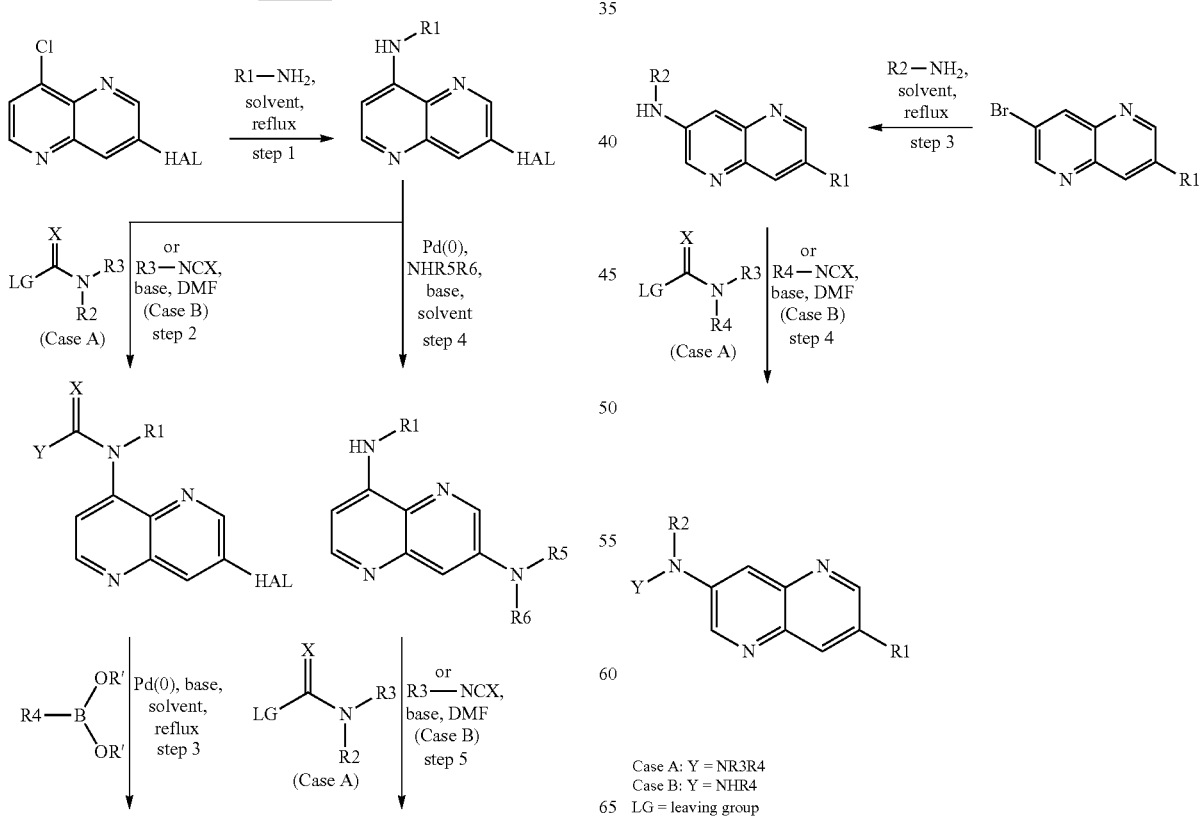

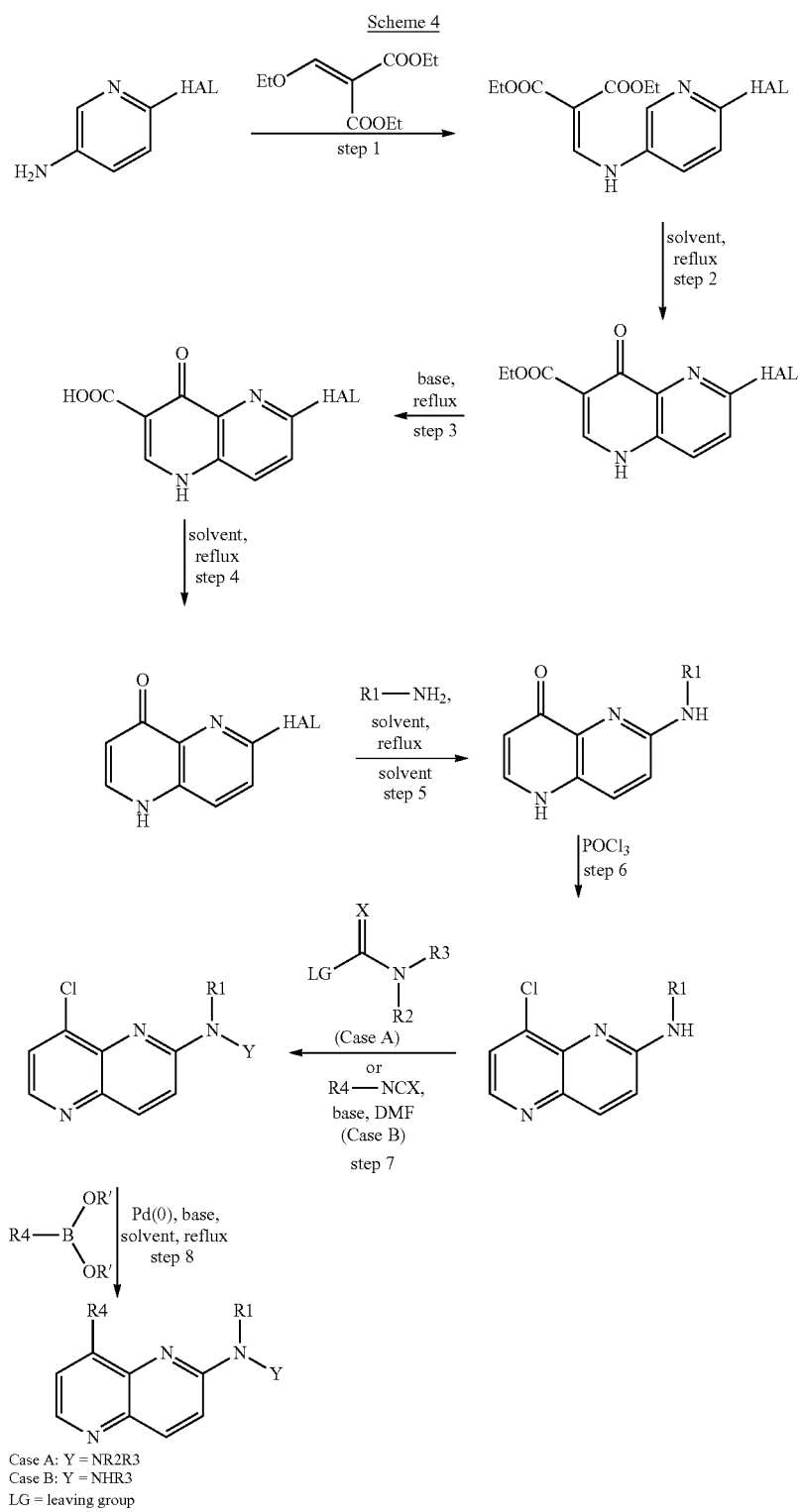

The starting materials are either commercially available or can be prepared by procedures known per se.

Any solvents and auxiliaries to be used, if appropriate, and the reaction parameters to be used, such as temperature and duration of the reaction, are known to the person skilled in the art by virtue of his expert knowledge.

The compounds below, which are evident from the statement of the respective chemical name from the survey hereinafter, were synthesized according to Synthesis Schemes 1-4. The analytical characterization of the compounds according to the invention was carried out by their melting points and/or by $^1$H-NMR spectroscopy at 300 K and/or mass spectroscopy.

The chemicals and solvents used were obtained commercially from conventional suppliers (Acros, Aldrich, Alfa Aesar, Apollo, Fluka, Maybridge, Merck, Sigma, TCI etc.) or synthesized.

EXAMPLES

The invention is to be explained in more detail by means of the following examples without being restricted thereto.

The chemical names of the substances were generated using the AutoNom 2000 Software (ISIS™/Draw 2.5 SP1; MDL).

Example 1

Reaction According to Scheme 1, Step 1

Example 1.1.1 and Example 1.1.2

3-Bromo-[1,5]naphthyridine-5-oxide and
3-bromo-1,5-naphthyridine-1-oxide

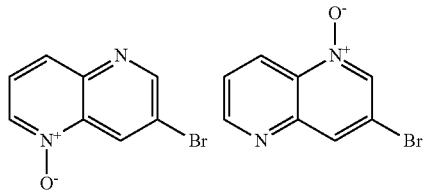

4.43 g (21.2 mmol, 1 eq) of 3-bromo-1,5-naphthyridine (W. Czuba, Recueil des Travaux Chimiques des Pays-Bas 1963, 82, 988-996) were introduced in 165 mL of methylene chloride. 5.23 g (21.2 mmol, 1 eq) of meta-chloroperbenzoic acid were then added portionwise at 0° C. The mixture was stirred at rt for 18 h. The mixture was washed with 1M aqueous NaOH solution and water. Organic layer was dried over Na$_2$SO$_4$, filtered and evaporated to dryness. The residue was purified by column chromatography using methylene chloride and then methylene chloride/ethanol: 98/2 as eluent. The solvent was evaporated to dryness to afford 3.08 g of 3-bromo-1,5-naphthyridine-5-oxide (pale yellow powder) with 64% yield and 1.00 g of 3-bromo-1,5-naphthyridine-1-oxide (yellow powder) with 21% yield.

3-Bromo-[1,5]naphthyridine-5-oxide

Yield: 3.08 g (64% of theory).
m.p.: 148-149° C.
$^1$H-NMR (DMSO-d$_6$, 400 MHz): δ =9.21 (d, 1H); 9.10 (d, 1H); 8.75 (d, 1H); 8.06 (d, 1H); 7.80 (dd, 1H) ppm.
MS: m/z 226 (M+H$^+$).

3-Bromo-[1,5]naphthyridine-1-oxide

Yield: 1.00 g (21% of theory).
m.p.: 153-154° C.
$^1$H-NMR (DMSO-d$_6$, 400 MHz): δ =9.12 (d, 1H); 9.03 (s, 1H); 8.86 (d, 1H); 8.36 (s, 1H); 7.94 (dd, 1H) ppm.
MS: m/z 226 (M+H$^+$).

Example 2

Reaction According to Scheme 1, Step 2

Example 2.1.1 and Example 2.1.2

7-Bromo-2-chloro-[1,5]naphthyridine and
7-Bromo-4-chloro-[1,5]naphthyridine

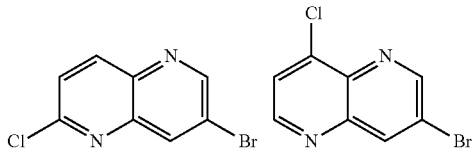

7.97 g (35.4 mmol, 1 eq) of 3-bromo-1,5-naphthyridine-5-oxide and 9.9 mL (106.2 mmol, 3 eq) of phosphorus oxychloride were introduced in 600 mL of methylene chloride. The mixture was stirred at reflux for 18 h. Methylene chloride was evaporated in part (¾). 1M aqueous NaOH solution was added carefully at 0° C. Aqueous layer was extracted with methylene chloride. Organic layers were dried over Na$_2$SO$_4$, filtered and evaporated to dryness. The residue was purified by column chromatography using methylene chloride as eluent. The solvent was evaporated to dryness to afford 1.97 g of 7-bromo-2-chloro-1,5-naphthyridine (white powder) with 22% yield and 4.16 g of 7-bromo-4-chloro-1,5-naphthyridine (white powder) with 48% yield.

7-Bromo-2-chloro-[1,5]naphthyridine

Yield: 1.97 g (22% of theory).
m.p.: 168-169° C.
$^1$H-NMR (DMSO-d$_6$, 400 MHz):=9.15 (d, 1H); 8.79 (d, 1H); 8.55 (d, 1H); 7.93 (d, 1H) ppm.
MS: m/z 245 (M+H$^+$).

7-Bromo-4-chloro-[1,5]naphthyridine

Yield: 4.16 g (48% of theory).
m.p.: 162-163° C.
$^1$H-NMR (DMSO-d$_6$, 400 MHz): δ =9.22 (d, 1H); 8.99 (d, 1H); 8.88 (d, 1H); 8.11 (d, 1H) ppm.
MS: m/z 245 (M+H$^+$).

Example 3

Reaction According to Scheme 1, Step 3

Example 3.1

7-Bromo-[1,5]naphthyridin-2-ylamine

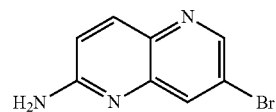

In a sealed reactor, 500 mg (1.23 mmol, 1 eq) of 7-bromo-2-chloro-1,5-naphthyridine and 7 mL (41.6 mmol, 33 eq) of 20% aqueous ammonia solution were introduced in 7 mL of dioxane. The mixture was stirred at 160° C. for 24 h. The mixture was allowed to reach rt and water was added. Aqueous layer was extracted with ethyl acetate. Organic layers were dried over Na$_2$SO$_4$, filtered and evaporated to dryness. The residue was purified by column chromatography using methylene chloride and then methylene chloride/ethanol: 98/2 as eluent. The solvent was evaporated to dryness to afford 220 mg of white powder with 80% yield.

Yield: 220 mg (80% of theory).
m.p.: 168-169° C.
$^1$H-NMR (DMSO-d$_6$, 400 MHz): δ =8.57 (d, 1H); 8.05 (d, 1H); 7.96 (d, 1H); 6.04 (d, 1H); 6.98 (s, 2H) ppm.
MS: m/z 225 (M+H$^+$).

Example 4

Reaction According to Scheme 1, Step 4

Example 4.1

1-(7-Bromo-[1,5]naphthyridin-2-yl)-3-tert-butyl-urea

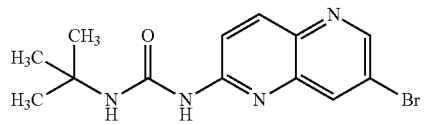 [SMILES: CC(C)(C)NC(=O)Nc1ccc2ncc(Br)cc2n1]

In a sealed reactor, 300 mg (1.34 mmol, 1 eq) of 7-bromo-[1,5]naphthyridin-2-ylamine and 305 μL (2.68 mmol, 2 eq) of tert-butyl isocyanate were introduced in 6 mL of pyridine. The mixture was stirred at 140° C. for 24 h. The mixture was allowed to reach rt and the solvent was removed under reduced pressure. The residue was purified by column chromatography using methylene chloride/ethanol: 96/4 as eluent. The solvent was evaporated to dryness to afford 398 mg of white powder with 92% yield.

Yield: 398 mg (92% of theory).
m.p.: >300° C.
$^1$H-NMR (DMSO-d$_6$, 400 MHz): δ =9.83 (s, 1H); 9.07 (s, 1H); 8.86 (d, 1H); 8.38 (d, 1H); 8.29 (d, 1H); 7.64 (d, 1H); 1.44 (s, 9H) ppm.
MS: m/z 323 (M+H$^+$); 325 ((M+2)+H$^+$).

The intermediates below were synthesized analogously to Example 4.1: (1-(7-Bromo-[1,5]naphthyridin-2-yl)-3-tert-butyl-urea).

Example 4.2

1-(7-Bromo-[1,5]naphthyridin-2-yl)-3-ethyl-urea

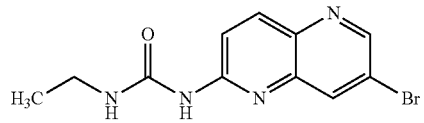 [SMILES: CCNC(=O)Nc1ccc2ncc(Br)cc2n1]

Yield: 102 mg (77% of theory).
m.p.: 225-226° C.

$^1$H-NMR (DMSO-d$_6$, 400 MHz): δ =9.99 (s, 1H); 9.12 (sl, 1H); 8.85 (d, 1H); 8.67 (d, 1H); 8.29 (d, 1H); 7.69 (d, 1H); 3.37-3.28 (m, 2H); 1.21 (t, 3H) ppm.
MS: m/z 295 (M+H$^+$); 297 ((M+2)+H$^+$).

Example 4.3

1-(7-Bromo-[1,5]naphthyridin-2-yl)-3-cyclopropyl-thiourea

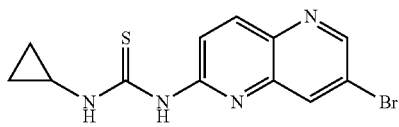 [SMILES: S=C(Nc1ccc2ncc(Br)cc2n1)NC1CC1]

Yield: 109 mg (58% of theory).
m.p.: 233-234° C.
$^1$H-NMR (DMSO-d$_6$, 400 MHz): δ =11.90 (d, 1H); 11.19 (s, 1H); 8.90 (d, 1H); 8.70 (d, 1H); 8.35 (d, 1H); 7.61 (d, 1H); 3.30-3.24 (m, 1H); 0.92-0.88 (m, 4H) ppm.
MS: m/z 324 (M+H$^+$).

Example 4.4

1-(7-Bromo-[1,5]naphthyridin-2-yl)-3-phenyl-urea

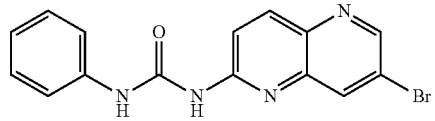 [SMILES: O=C(Nc1ccccc1)Nc1ccc2ncc(Br)cc2n1]

Yield: 130 mg (71% of theory)
m.p.: 324-325° C.
$^1$H-NMR (DMSO-d$_6$, 400 MHz): δ =11.45 (s, 1H); 10.36 (s, 1H); 8.92 (d, 1H); 8.82 (d, 1H); 8.39 (d, 1H); 7.79-7.72 (m, 3H); 7.40 (t, 2H); 7.15-7.11 (m, 1H) ppm.
MS: m/z 341 (M+H$^+$); 345 ((M+2)+H$^+$).

Example 4.5

1-(7-Bromo-[1,5]naphthyridin-2-yl)-3-benzyl-urea

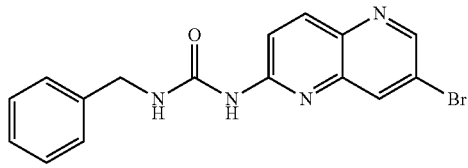 [SMILES: O=C(NCc1ccccc1)Nc1ccc2ncc(Br)cc2n1]

Yield: 144 mg (90% of theory)
m.p.: 250-252° C.
$^1$H-NMR (DMSO-d$_6$, 400 MHz): δ =10.13 (s, 1H); 9.63 (sl, 1H); 8.86 (d, 1H); 8.66 (d, 1H); 8.33 (d, 1H); 7.63 (d, 1H); 7.36-7.28 (m, 5H); 4.54 (d, 2H).
MS: m/z 357 (M+H$^+$); 359 ((M+2)+H$^+$).

Example 4.6

1-(7-Bromo-[1,5]naphthyridin-2-yl)-3-phenethyl-urea

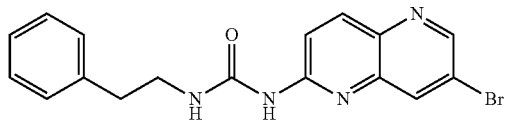 [SMILES: O=C(NCCc1ccccc1)Nc1ccc2ncc(Br)cc2n1]

Under argon atmosphere, 201 mg (897 μmol, 1 eq) of 7-bromo-[1,5]naphthyridin-2-ylamine and 294 mg (993 μmol, 1.1 eq) of triphosgene were introduced in 10 mL of pyridine at 0° C. The mixture was stirred at reflux for 1 h. The mixture was allowed to reach rt and 238 μL (1.89 mmol, 2.1 eq) of 2-phenylethylamine were added. The mixture was stirred at reflux for 1 h. The mixture was allowed to reach rt and water was added. Aqueous layer was extracted with methylene chloride. Organic layers were dried over $Na_2SO_4$, filtered and evaporated to dryness. The residue was purified by column chromatography using methylene chloride/ethanol: 96/4 as eluent. The solvent was evaporated to dryness to afford 80 mg of yellow powder with 24% yield.

Yield: 80 mg (24% of theory).

m.p.: 245-246° C.

$^1$H-NMR (DMSO-$d_6$, 400 MHz): δ=10.03 (s, 1H); 9.25 (t, 1H); 8.80 (d, 1H); 8.23 (d, 1H); 8.10 (d, 1H); 7.48 (d, 1H); 7.36-7.24 (m, 5H); 3.58 (q, 2H); 2.88 (t, 2H) ppm.

MS: m/z 371 (M+H$^+$); 373 ((M+2)+H$^+$).

Example 5

Reaction According to Scheme 1, Step 5

Example 5.1

1-Ethyl-3-[7-(4-methoxy-phenyl)-[1,5]naphthyridin-2-yl]urea (1)

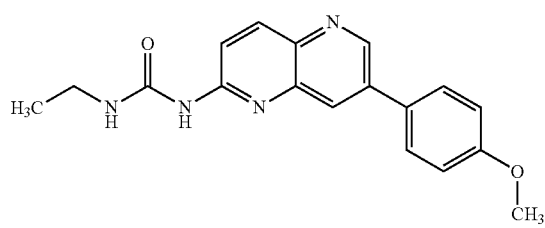 [SMILES: CCNC(=O)Nc1ccc2ncc(-c3ccc(OC)cc3)cc2n1]

Under argon atmosphere, 100 mg (338 μmol, 1 eq) of 1-(7-bromo-[1,5]naphthyridin-2-yl)-3-ethyl-urea, 103 mg (676 μmol, 2 eq) of 4-methoxyphenylboronic acid, 72 mg (676 μmol, 2 eq) of sodium carbonate and 29 mg (25 μmol, 0.07 eq) of tetrakis(triphenylphosphine)palladium were introduced in 10 mL of a dioxane/$H_2O$ mixture (8/2). The mixture was stirred at 90° C. for 2 h. The mixture was allowed to reach rt, hydrolysed and filtrated over Celite. The filtrate was extracted by methylene chloride. Organic layer was dried over $Na_2SO_4$, filtered and evaporated to dryness. The residue was purified by column chromatography using methylene chloride/ethanol: 99/1 and then methylene chloride/ethanol: 97/3 as eluent. The solvent was evaporated to dryness to afford 56 mg of orange powder with 51% yield.

Yield: 56 mg (51% of theory).

m.p.: 264-265° C.

$^1$H-NMR (DMSO-$d_6$, 400 MHz): δ=9.89 (s, 1H); 9.33 (bs, 1H); 9.12 (d, 1H); 8.46 (d, 1H); 8.46 (d, 1H); 7.92 (d, 2H); 7.51 (d, 1H); 7.15 (d, 2H); 3.87 (s, 1H); 3.33 (q, 2H); 1.23 (t, 3H) ppm.

MS: m/z 323 (M+H$^+$).

The examples below were synthesized analogously to Example 5.1: 1-Ethyl-3-[7-(4-methoxy-phenyl)-[1,5]naphthyridin-2-yl]-urea (1).

Example 5.2

1-[7-(3,4-Dimethoxy-phenyl)-[1,5]naphthyridin-2-yl]-3-ethyl-urea (2)

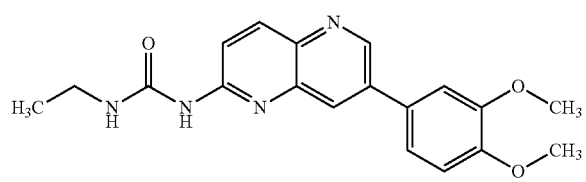 [SMILES: CCNC(=O)Nc1ccc2ncc(-c3ccc(OC)c(OC)c3)cc2n1]

Yield: 58 mg (49% of theory).

m.p.: 218-219° C.

$^1$H-NMR (DMSO-$d_6$, 400 MHz): δ=9.88 (s, 1H); 9.30 (t, 1H); 9.16 (d, 1H); 8.47 (d, 1H); 8.29 (d, 1H); 7.57-7.45 (m, 3H); 7.16 (d, 1H); 3.94 (s, 3H); 3.87 (s, 3H); 3.29-3.16 (m, 2H); 1.23 (t, 3H) ppm.

MS: m/z 353 (M+H$^+$).

Example 5.3

1-tert-Butyl-3-[7-(3,4-dimethoxy-phenyl)-[1,5]naphthyridin-2-yl]-urea (3)

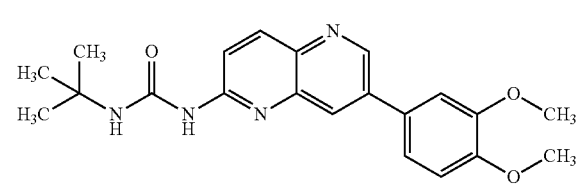 [SMILES: COc1ccc(-c2cnc3ccc(NC(=O)NC(C)(C)C)nc3c2)cc1OC]

Yield: 42 mg (35% of theory).

m.p.: 279-280° C.

$^1$H-NMR (DMSO-$d_6$, 400 MHz): δ=9.71 (s, 1H); 9.33 (s, 1H); 9.13 (d, 1H); 8.29 (d, 1H); 8.19 (d, 1H); 7.57 (d, 1H); 7.49-7.44 (m, 2H); 7.16 (d, 1H); 3.93 (s, 3H); 3.87 (s, 3H); 1.46 (t, 9H) ppm.

MS: m/z 381 (M+H$^+$).

Example 5.4

1-tert-Butyl-3-[7-(4-hydroxy-3-methoxy-phenyl)-[1,5]naphthyridin-2-yl]-urea (4)

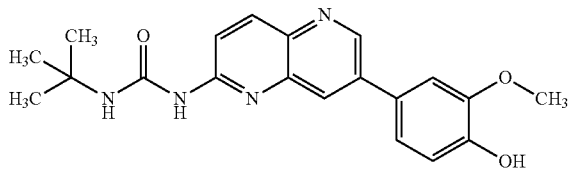 [SMILES: COc1cc(-c2cnc3ccc(NC(=O)NC(C)(C)C)nc3c2)ccc1O]

Under argon atmosphere, 100 mg (309 μmol, 1 eq) of 1-(7-bromo-[1,5]naphthyridin-2-yl)-3-tert-butyl-urea, 230 mg (927 μmol, 3 eq) of 2-methoxy-4-(4,4,5,5-tetramethyl-1,3,2-dioxaborolan-2-yl)phenol, 196 mg (1.854 mmol, 6 eq) of sodium carbonate and 50 mg (43 μmol, 0.14 eq) of tetrakis(triphenylphosphine)palladium were introduced in 11 mL of a dimethylformamide/H$_2$O mixture (10/1). The mixture was stirred at 80° C. for 16 h. The mixture was allowed to reach rt, and adjusted at pH 7 by adding 1M HCl aqueous solution. The filtrate was extracted by methylene chloride. Organic layer was dried over Na$_2$SO$_4$, filtered and evaporated to dryness. The residue was purified by column chromatography using methylene chloride/ethanol: 98/2 as eluent. The solvent was evaporated to dryness to afford 62 mg of yellow powder with 53% yield.

Yield: 62 mg (53% of theory).
m.p.: 286-287° C.
$^1$H-NMR (DMSO-d$_6$, 400 MHz): δ =9.69 (s, 1H); 9.42 (s, 1H); 9.33 (s, 1H); 9.11 (d, 1H); 8.27 (d, 1H); 8.15 (d, 1H); 7.55 (d, 1H); 7.46 (d, 1H); 7.34 (dd, 1H); 6.98 (d, 1H); 3.94 (s, 3H); 1.46 (t, 9H) ppm.
MS: m/z 367 (M+H$^+$).

The examples below were synthesized analogously to Example 5.4: 1-tert-Butyl-3-[7-(4-hydroxy-3-methoxy-phenyl)-[1,5]naphthyridin-2-yl]-urea (4)

Example 5.5

1-[7-(1-Methyl-1H-pyrazol-4-yl)-[1,5]naphthyridin-2-yl]-3-phenethyl-urea (5)

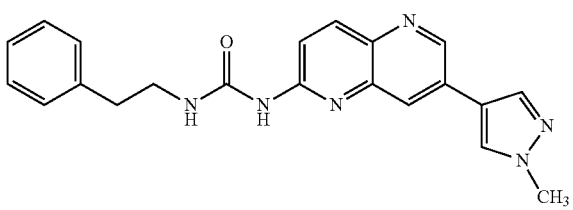

Yield: 50 mg (71% of theory).
m.p.: 237-238° C.
$^1$H-NMR (DMSO-d$_6$, 400 MHz): δ =9.92 (s, 1H); 9.39 (bs, 1H); 9.07 (d, 1H); 8.45 (s, 1H); 8.22 (d, 1H); 8.15 (s, 1H); 8.03 (d, 1H); 7.44 (d, 1H); 7.39-7.22 (m, 5H); 3.98 (s, 3H); 3.62 (q, 2H); 2.94 (t, 2H) ppm.
MS: m/z 373 (M+H$^+$).

Example 5.6

1-tert-Butyl-3-[7-(1-methyl-1H-pyrazol-4-yl)-[1,5]naphthyridin-2-yl]-urea (26)

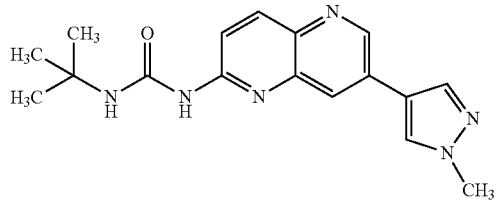 [SMILES: Cn1cc(-c2cnc3ccc(NC(=O)NC(C)(C)C)nc3c2)cn1]

Yield: 40 mg (37% of theory)
$^1$H-NMR (DMSO-d$_6$, 600 MHz): δ =9.62 (s, 1H); 9.26 (s, 1H); 9.04 (s, 1H); 8.46 (s, 1H); 8.18 (d, 1H); 8.16 (s, 1H); 8.07 (s, 1H); 7.46 (d, 1H); 3.92 (s, 3H); 1.43 (s, 9H) ppm.
MS: m/z 325 (M+H$^+$).

Example 5.7

1-[7-(1-Methyl-1H-pyrazol-4-yl)-[1,5]naphthyridin-2-yl]-3-phenyl-urea (27)

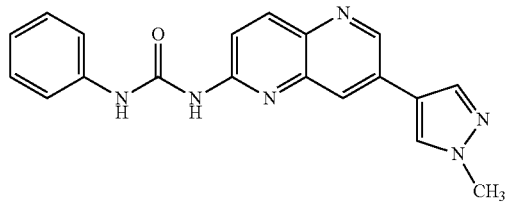

Yield: 25 mg (78% of theory)
m.p.: 270-271° C.
$^1$H-NMR (DMSO-d$_6$, 400 MHz): δ =11.73 (s, 1H); 10.23 (s, 1H); 9.15 (s, 1H); 8.57 (s, 1H); 8.45 (s, 1H); 8.34-8.29 (m, 2H); 7.78 (d, 2H); 7.58 (d, 1H); 7.42 (t, 2H); 7.14-7.10 (m, 1H); 3.98 (s, 3H) ppm.
MS: m/z 345 (M+H$^+$).

Example 5.8

1-Benzyl-3-[7-(1-methyl-1H-pyrazol-4-yl)-[1,5]naphthyridin-2-yl]-urea (28)

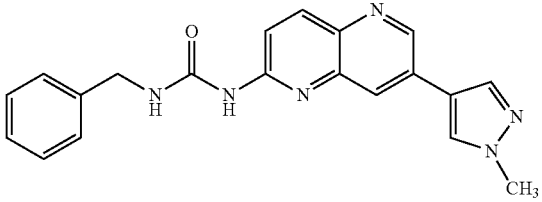 [SMILES: Cn1cc(-c2cnc3ccc(NC(=O)NCc4ccccc4)nc3c2)cn1]

Yield: 40 mg (60% of theory)
m.p.: 257-258° C.

¹H-NMR (DMSO-d₆, 400 MHz): δ=10.00 (s, 1H); 9.75 (m, 1H); 9.10 (d, 1H); 8.46 (s, 1H); 8.32 (d, 1H); 8.26 (d, 1H); 8.15 (s, 1H); 7,53 (d, 1H); 7.44-7.28 (m, 5H); 4.57 (d, 2H); 3.95 (s, 3H) ppm.

MS: m/z 359 (M+H⁺).

Example 5.9

1-[7-(1-Methyl-1H-pyrazol-4-yl)-[1,5]naphthyridin-2-yl]-3-(4-phenyl-butyl)-urea (29)

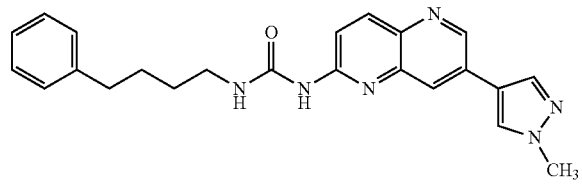 [SMILES: Cn1cc(-c2cnc3ccc(NC(=O)NCCCCc4ccccc4)nc3c2)cn1]

Yield: 32 mg (43% of theory)

¹H-NMR (DMSO-d₆, 600 MHz): δ=9.80 (s, 1H); 9.26 (s, 1H); 9.04 (s, 1H); 8.40 (s, 1H); 8.23 (s, 1H); 8.19 (d, 1H); 8.10 (s, 1H); 7,45 (s, 1H); 7.25-7.19 (m, 4H); 7.13 (t, 1H); 3.92 (s, 3H) 3.33 (t, 2H); 2.65 (t, 2H); 1.72-1.56 (dm, 4H); ppm.

MS: m/z 401 (M+H⁺).

Example 6

Reaction According to Scheme 1, Step 6

Example 6.1

N*7*-(3,4,5-Trimethoxy-phenyl)-[1,5]naphthyridine-2,7-diamine

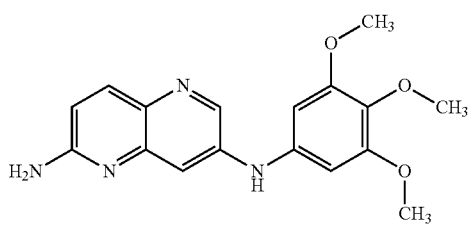 [SMILES: COc1cc(Nc2cnc3ccc(N)nc3c2)cc(OC)c1OC]

Under argon atmosphere, 200 mg (892 µmol, 1 eq) of 7-bromo-1,5-naphthyridin-2-ylamine, 196.3 mg (1.07 mmol, 1.2 eq) of 3,4,5-trimethoxyaniline, 2 mg (2.3 µmol, 0.0025 eq) tris(dibenzylideneacetone)dipalladium, 4 mg (6.7 µmol, 0.0075 eq) 2,2'-bis(diphenylphosphino)-1,1'-binaphtyl and 120 mg (1.24 mmol, 1.4 eq) of sodium terbutoxide were introduced in 6 mL of toluene. The mixture was stirred at 80° C. for 24 h. The mixture was allowed to reach it and water was added. Aqueous layer was extracted with methylene chloride. Organic layers were dried over Na₂SO₄, filtered and evaporated to dryness. The residue was purified by column chromatography using methylene chloride/ethanol: 96/4 as eluent. The solvent was evaporated to dryness to afford 50 mg of yellow powder with 17% yield.

Yield: 50 mg (17% of theory).

m.p.: 192-194° C.

¹H-NMR (DMSO-d₆, 400 MHz): δ=8.58 (s, 1H); 8.32 (d, 1H); 7.79 (d, 1H); 7.33 (d, 1H); 6.72 (d, 1H); 6.56 (s, 2H); 6.52 (s, 2H); 3.79 (s, 6H); 3.67 (s, 3H) ppm.

MS: m/z 327 (M+H⁺).

Example 7

Reaction According to Scheme 1, Step 7

Example 7.1

1-Ethyl-3-[7-(3,4,5-trimethoxy-phenylamino)-[1,5]naphthyridin-2-yl]-thiourea (6)

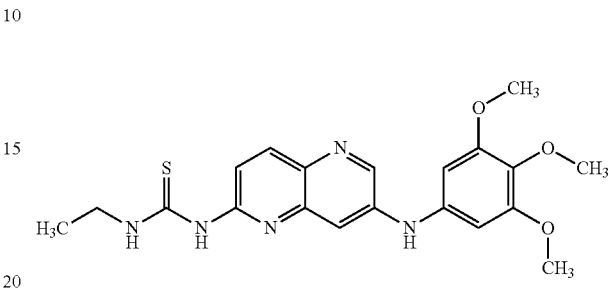

In a sealed reactor, 88 mg (269 µmol, 1 eq) of N*7*-(3,4,5-trimethoxy-phenyl)-[1,5]naphthyridine-2,7-diamine and 48 µL (538 µmol, 2 eq) of ethyl isothiocyanate were introduced in 3 mL of pyridine. The mixture was stirred at 140° C. for 24 h. The mixture was allowed to reach rt and the solvent was removed under reduced pressure. The residue was purified by column chromatography using methylene chloride/ethanol: 96/4 as eluent. The solvent was evaporated to dryness to afford 56 mg of yellow powder with 51% yield.

Yield: 56 mg (51% of theory).

m.p.: 237-238° C.

¹H-NMR (DMSO-d₆, 400 MHz): δ=12.21 (t, 1H); 10.84 (s, 1H); 8.95 (s, 1H); 8.59 (d, 1H); 8.15 (d, 1H); 7.79 (d, 1H); 7.27 (d, 1H); 6.61 (s, 2H); 3.82 (s, 6H); 3.72-3.67 (m, 5H); 1.28 (t, 3H) ppm.

MS: m/z 414 (M+H⁺).

Example 8

Reaction According to Scheme 2, Step 1

Example 8

7-Bromo-[1,5]naphthyridin-4-ylamine

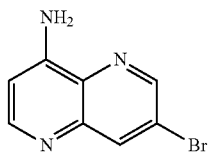 [SMILES: Nc1ccnc2cc(Br)cnc12]

In a sealed reactor, 500 mg (2.04 mmol, 1 eq) of 7-bromo-4-chloro-1,5-naphthyridine (G. B. Barlin et al. *Aust. J. Chem.* 1985, 38, 459-465) and 12 mL (71.3 mmol, 35 eq) of 20% aqueous ammonia solution were introduced in 12 mL of dioxane. The mixture was stirred at 160° C. for 24 h. The mixture was allowed to reach rt and water was added. Aqueous layer was extracted with ethyl acetate. Organic layers were dried over Na₂SO₄, filtered and evaporated to dryness. The residue was purified by column chromatography using methylene chloride and then methylene chloride/ethanol:

98/2 as eluent. The solvent was evaporated to dryness to afford 350 mg of white powder with 76% yield.

Yield: 350 mg (76% of theory).
m.p.: 168-169° C.
$^1$H-NMR (DMSO-d$_6$, 400 MHz): δ=8.82 (d, 1H); 8.43 (d, 1H); 8.40 (d, 1H); 7.08 (s, 2H); 6.79 (d, 1H) ppm.
MS: m/z 225 (M+H$^+$).

Example 9

Reaction According to Scheme 2, Step 2

Example 9.1

1-(7-Bromo-[1,5]naphthyridin-4-yl)-3-tert-butyl-urea

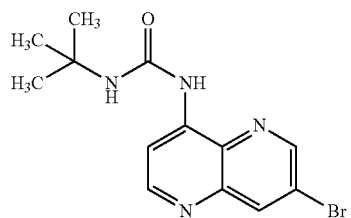 [SMILES: CC(C)(C)NC(=O)Nc1ccnc2cc(Br)cnc12]

In a sealed reactor, 500 mg (2.23 mmol, 1 eq) of 7-bromo-1,5-naphthyridin-4-ylamine and 508 µL (4.46 mmol, 2 eq) of tert-butyl isocyanate were introduced in 5 mL of pyridine. The mixture was stirred at 140° C. for 24 h. The mixture was allowed to reach rt and the solvent was removed under reduced pressure. The residue was purified by column chromatography using methylene chloride/ethanol: 99/1 as eluent. The solvent was evaporated to dryness to afford 540 mg of white powder with 75% yield.

Yield: 540 mg (75% of theory).
m.p.: 192-193° C.
$^1$H-NMR (DMSO-d$_6$, 400 MHz): δ=9.65 (s, 1H); 8.98 (d, 1H); 8.74 (d, 1H); 8.66 (d, 1H); 8.42 (d, 1H); 7.60 (s, 1H); 1.36 (s, 9H) ppm.
MS: m/z 323 (M+H$^+$); 325 ((M+2)+H$^+$).

The examples below were synthesized analogously to Example 9.1: 1-(7-Bromo-[1,5]naphthyridin-4-yl)-3-tert-butyl-urea.

Example 9.2

1-(7-Bromo-[1,5]naphthyridin-4-yl)-3-ethyl-urea

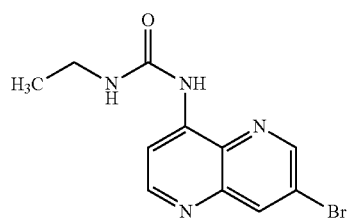 [SMILES: CCNC(=O)Nc1ccnc2cc(Br)cnc12]

Yield: 95 mg (84% of theory).
m.p.: 222-223° C.
$^1$H-NMR (DMSO-d$_6$, 400 MHz): δ=9.69 (s, 1H); 9.01 (d, 1H); 8.77 (d, 1H); 8.68 (d, 1H); 8.44 (d, 1H); 7.67 (t, 1H); 3.25-3.14 (m, 2H); 1.13 (t, 3H) ppm.
MS: m/z 295 (M+H$^+$); 297 ((M+2)+H$^+$).

Example 9.3

1-(7-Bromo-[1,5]naphthyridin-4-yl)-3-cyclohexyl-urea

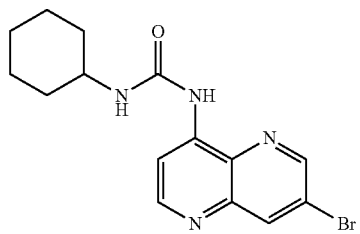 [SMILES: O=C(Nc1ccnc2cc(Br)cnc12)NC1CCCCC1]

Yield: 129 mg (55% of theory).
m.p.: 179-180° C.
$^1$H-NMR (DMSO-d$_6$, 400 MHz): δ=9.69 (s, 1H); 9.00 (d, 1H); 8.77 (d, 1H); 8.67 (d, 1H); 8.43 (d, 1H); 7.68 (d, 1H); 3.59-3.57 (m, 1H); 0.92-1.91 (m, 10H) ppm.
MS: m/z 349 (M+H$^+$); 351 ((M+2)+H$^+$).

Example 9.4

1-(7-Bromo-[1,5]naphthyridin-4-yl)-3-phenyl-urea

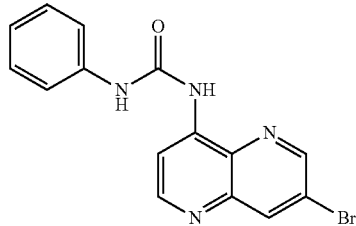 [SMILES: O=C(Nc1ccccc1)Nc1ccnc2cc(Br)cnc12]

Yield: 202 mg (66% of theory).
m.p.: 195-196° C.
$^1$H-NMR (DMSO-d$_6$, 400 MHz): δ=10.08 (s, 1H); 10.04 (s, 1H); 9.08 (d, 1H); 8.86 (d, 1H); 8.74 (d, 1H); 8.50 (d, 1H); 7.57 (d, 2H); 7.38 (dd, 2H); 7.08 (t, 1H) ppm.
MS: m/z 343 (M+H$^+$); 345 ((M+2)+H$^+$).

Example 9.5

1-Allyl-3-(7-bromo-[1,5]naphthyridin-4-yl)-urea

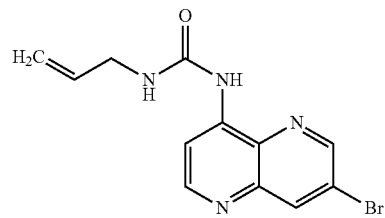

Yield: 140 mg (51% of theory).
m.p.: 179-180° C.

¹H-NMR (DMSO-d₆, 400 MHz): δ=9.85 (s, 1H); 9.02 (d, 1H); 8.78 (d, 1H); 8.69 (d, 1H); 8.44 (d, 1H); 7.80 (t, 1H); 5.98-5.87 (m, 1H); 5.26 (dq, 1H); 5.15 (dq, 1H); 3.87-3.82 (m, 2H) ppm.
MS: m/z 307 (M+H⁺); 309 ((M+2)+H⁺).

Example 9.6

1-(7-Bromo-[1,5]naphthyridin-4-yl)-3-isopropyl-urea

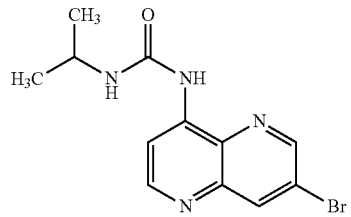 [SMILES: CC(C)NC(=O)Nc1ccnc2cc(Br)cnc12]

Yield: 150 mg (72% of theory)
m.p.: 175-177° C.
¹H-NMR (DMSO-d₆, 400 MHz): δ=9.63 (s, 1H); 9.00 (d, 1H); 8.77 (d, 1H); 8.68 (d, 1H); 8.43 (d, 1H); 7.64 (d, 1H); 3.89-3.82 (m, 1H); 1.17 (d, 6H).
MS: m/z 309 (M+H⁺); 311 ((M+2)+H⁺).

Example 9.7

1-(7-Bromo-[1,5]naphthyridin-4-yl)-3-benzyl-urea

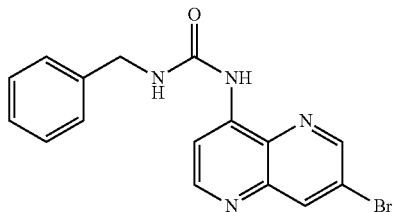 [SMILES: O=C(NCc1ccccc1)Nc1ccnc2cc(Br)cnc12]

Yield: 232 mg (98% of theory)
m.p.: 138-140° C.
¹H-NMR (DMSO-d₆, 400 MHz): δ=9.87 (s, 1H); 9.01 (d, 1H); 8.78 (d, 1H); 8.69 (d, 1H); 8.46 (d, 1H); 8.16 (t, 1H); 7.39-7.27 (m, 5H); 4.35 (d, 2H).
MS: m/z 357 (M+H⁺); 359 ((M+2)+H⁺).

Example 9.8

1-(7-Bromo-[1,5]naphthyridin-4-yl)-3-butyl-urea

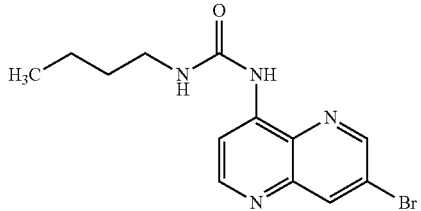 [SMILES: CCCCNC(=O)Nc1ccnc2cc(Br)cnc12]

Yield: 50 mg (23% of theory)
m.p.: 158-160° C.
¹H-NMR (DMSO-d₆, 400 MHz): δ=9.73 (s, 1H); 9.01 (d, 1H); 8.77 (d, 1H); 8.68 (d, 1H); 8.44 (d, 1H); 7.67 (t, 1H); 3.18 (dt, 2H); 1.51-1.36 (m, 4H); 0.95 (t, 3H).
MS: m/z 323 (M+H⁺); 325 ((M+2)+H⁺).

Example 9.9

1-(7-Bromo-[1,5]naphthyridin-4-yl)-3-cyclopropyl-urea

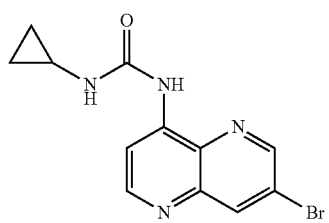 [SMILES: O=C(Nc1ccnc2cc(Br)cnc12)NC1CC1]

Under argon atmosphere, 217 mg (968 μmol, 1 eq) of 7-bromo-[1,5]naphthyridin-4-ylamine, 5 mL (34.9 mmol, 27 eq) of triethylamine and 316 mg (1.07 mmol, 1.1 eq) of triphosgene were introduced in 25 mL of methylene chloride at 0° C. The mixture was stirred at reflux for 1 h. The mixture was allowed to reach rt and 148 μL (2.2 mmol, 2.1 eq) of cyclopropylamine were added. The mixture was stirred at reflux for 1.5 h. The mixture was allowed to reach rt and water was added. Aqueous layer was extracted with methylene chloride. Organic layers were dried over Na₂SO₄, filtered and evaporated to dryness. The residue was purified by column chromatography using methylene chloride/ethanol: 96/4 as eluent. The solvent was evaporated to dryness to afford 196 mg of brown powder with 65% yield.
Yield: 196 mg (65% of theory).
m.p.: 205-206° C.
¹H-NMR (DMSO-d₆, 400 MHz): δ=9.62 (s, 1H); 9.00 (d, 1H); 8.78 (d, 1H); 8.68 (d, 1H); 8.43 (d, 1H); 7.82 (s, 1H); 2.69-2.63 (m, 1H); 0.72 and 0.47 (bs, 4H) ppm.
MS: m/z 307 (M+H⁺); 309 ((M+2)+H⁺).
The examples below were synthesized analogously to Example 9.6: 1-(7-Bromo-[1,5]naphthyridin-4-yl)-3-cyclopropyl-urea.

Example 9.10

1-(7-Bromo-[1,5]naphthyridin-4-yl)-3-(4-phenyl-butyl)-urea

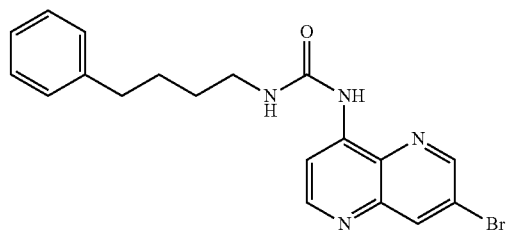 [SMILES: O=C(NCCCCc1ccccc1)Nc1ccnc2cc(Br)cnc12]

Yield: 161 mg (60% of theory).
m.p.: 115-116° C.

¹H-NMR (DMSO-d₆, 400 MHz): δ=9.72 (s, 1H); 9.00 (d, 1H); 8.76 (d, 1H); 8.68 (d, 1H); 8.43 (d, 1H); 7.67 (t, 1H); 7.33-7.19 (m, 5H); 3.21 (q, 2H); 2.64 (t, 2H); 1.69-1.61 (m, 2H); 1.55-1.49 (m, 2H) ppm.

MS: m/z 399 (M+H⁺); 401 ((M+2)+H⁺).

Example 9.11

1-(7-Bromo-[1,5]naphthyridin-4-yl)-3-cyclobutyl-urea

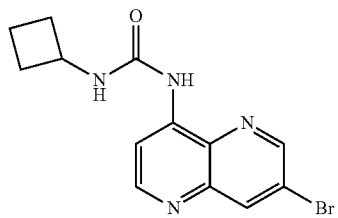 [SMILES: O=C(Nc1ccnc2cc(Br)cnc12)NC1CCC1]

Yield: 202 mg (70% of theory).
m.p.: 201-202° C.
¹H-NMR (DMSO-d₆, 400 MHz): δ=9.62 (s, 1H); 9.01 (d, 1H); 8.77 (d, 1H); 8.68 (d, 1H); 8.41 (d, 1H); 7.98 (d, 1H); 4.25-4.16 (m, 1H); 2.32-2.44 and 1.95-1.84 (m, 4H); 1.75-1.64 (m, 2H) ppm.
MS: m/z 321 (M+H⁺); 323 ((M+2)+H⁺).

Example 9.12

1-(7-Bromo-[1,5]naphthyridin-4-yl)-3-propyl-urea

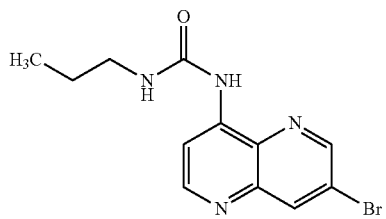 [SMILES: CCCNC(=O)Nc1ccnc2cc(Br)cnc12]

Yield: 151 mg (52% of theory).
m.p.: 173-174° C.
¹H-NMR (DMSO-d₆, 400 MHz): δ=9.72 (s, 1H); 8.99 (d, 1H); 8.76 (d, 1H); 8.66 (d, 1H); 8.44 (d, 1H); 7.68 (t, 1H); 3.15 (q, 2H); 1.57-1.47 (m, 2H); 0.96 (t, 3H) ppm.

MS: m/z 309 (M+H⁺); 311 ((M+2)+H⁺).

Example 9.13

1-(7-Bromo-[1,5]naphthyridin-4-yl)-3-(2,2,2-trifluoro-ethyl)-urea

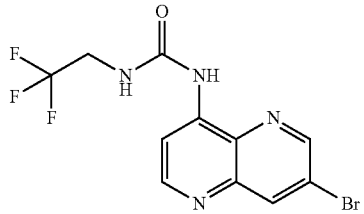 [SMILES: O=C(NCC(F)(F)F)Nc1ccnc2cc(Br)cnc12]

Yield: 102 mg (56% of theory).
m.p.: 181-182° C.
¹H-NMR (DMSO-d₆, 400 MHz): δ=9.99 (s, 1H); 9.04 (d, 1H); 8.82 (d, 1H); 8.71 (d, 1H); 8.43 (d, 1H); 8.30 (t, 1H); 4.13-4.03 (m, 2H) ppm.
MS: m/z 349 (M+H⁺); 351 ((M+2)+H⁺).

Example 9.14

1-(7-Bromo-[1,5]naphthyridin-4-yl)-3-(2-phenyl-ethyl)-urea

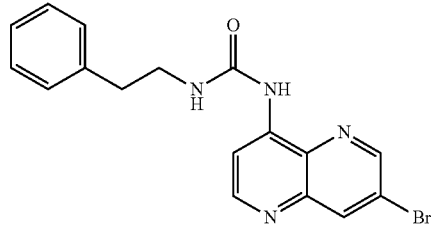 [SMILES: O=C(NCCc1ccccc1)Nc1ccnc2cc(Br)cnc12]

Yield: 119 mg (65% of theory)
m.p.: 119-121° C.
¹H-NMR (DMSO-d₆, 400 MHz): δ=9.89 (s, 1H); 9.00 (d, 1H); 8.75 (d, 1H); 8.67 (d, 1H); 8.45 (d, 1H); 7.85 (t, 1H); 7.35-7.21 (m, 5H); 3.45 (dt, 2H); 2.86 (t, 2H).
MS: m/z 371 (M+H⁺); 373 ((M+2)+H⁺).

Example 9.15

1-(7-Bromo-[1,5]naphthyridin-4-yl)-3-cyclopentyl-urea

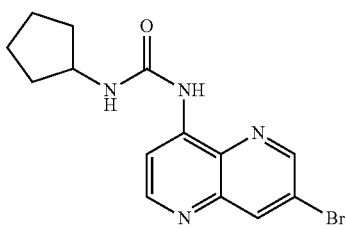 [SMILES: O=C(Nc1ccnc2cc(Br)cnc12)NC1CCCC1]

Yield: 55 mg (28% of theory)
m.p.: 183-185° C.

¹H-NMR (DMSO-d₆, 400 MHz): δ=9.65 (s, 1H); 9.00 (d, 1H); 8.75 (d, 1H); 8.66 (d, 1H); 8.42 (d, 1H); 7.82 (d, 1H); 4.15-4.06 (m, 1H); 1.95-1.24 (m, 8H).

MS: m/z 335 (M+H⁺); 337 ((M+2)+H⁺).

Example 9.16

1-(7-Bromo-[1,5]naphthyridin-4-yl)-3-(3,3-difluoro-cyclobutyl)-urea

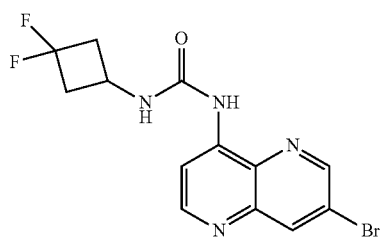 [SMILES: O=C(Nc1ccnc2cc(Br)cnc12)NC1CC(F)(F)C1]

A solution of 424 mg (2.1 mmol, 1 eq) of 4-nitrophenyl chloroformiate in 5 mL dry acetonitrile was cooled to −5° C. by means of an ice/NaCl mixture. To this solution was slowly added 300 mg (2.1 mmol, 1 eq) of 3,3-difluorocyclobutylamine hydrochloride in while maintaining the temperature below 0° C. Then a solution of 0.59 mL (4.2 mmol, 2 eq) of triethylamine in 5 mL of acetonitrile was added maintaining the temperature below 0° C. After the addition was completed, the reaction mixture was stirred at room temperature overnight. Water was added and aqueous layer was extracted with methylene chloride. Organic layers were dried over Na₂SO₄, filtered and evaporated to dryness. The residue was purified by column chromatography using methylene chloride/ethanol: 96/4 as eluent. The solvent was evaporated to dryness to afford 200 mg of white powder with 34% yield.

A mixture of 200 mg (734 mmol, 1 eq) of N-3,3-difluoro-cyclobutylcarbamic acid 4-nitro-phenylester and 82 mg (367 μmol, 0.5 eq) of 7-bromo-[1,5]naphthyridin-4-ylamine, and 10 μL (7.34 mmol, 0.1 eq) of triethylamine in 2 mL dry THF was stirred at 60° C. for 24 hours. The reaction mixture was then cooled to room temperature and evaporated to dryness. The residue was purified by column chromatography using methylene chloride/ethanol: 96/4 as eluent. The solvent was evaporated to dryness to afford 101 mg of white powder with 77% yield.

Yield: 101 mg (77% of theory).

m.p.: 184-185° C.

¹H-NMR (DMSO-d₆, 400 MHz): δ=9.70 (s, 1H); 9.03 (d, 1H); 8.80 (d, 1H); 8.70 (d, 1H); 8.41 (d, 1H); 8.23 (d, 1H); 4.11 (bs, 1H); 3.09-2.64 (m, 4H) ppm.

MS: m/z 358 (M+H⁺)

The examples below were synthesized analogously to Example 9.11: 1-(7-Bromo-[1,5]naphthyridin-4-yl)-3-(3,3-difluoro-cyclobutyl)-urea.

Example 9.17

1-(7-Bromo-[1,5]naphthyridin-4-yl)-3-hexyl-urea

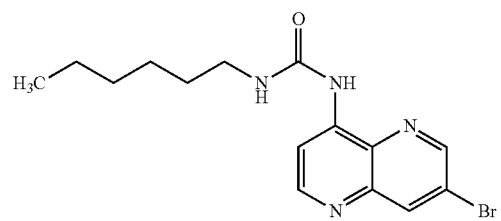 [SMILES: CCCCCCNC(=O)Nc1ccnc2cc(Br)cnc12]

Yield: 157 mg (62% of theory).

m.p.: 186-187° C.

¹H-NMR (DMSO-d₆, 400 MHz): δ=9.72 (s, 1H); 9.00 (d, 1H); 8.76 (d, 1H); 8.67 (d, 1H); 8.44 (d, 1H); 7.66 (t, 1H); 3.17 (dt, 2H); 1.51-1.47 (m, 2H); 1.42-1.34 (m, 6H); 0.92 (t, 3H) ppm.

MS: m/z 352 (M+H⁺).

Example 10

Reaction According to Scheme 2, Step 3

Example 10.1

1-[7-(3,4-Dimethoxy-phenyl)-[1,5]naphthyridin-4-yl]-3-ethyl-urea (7)

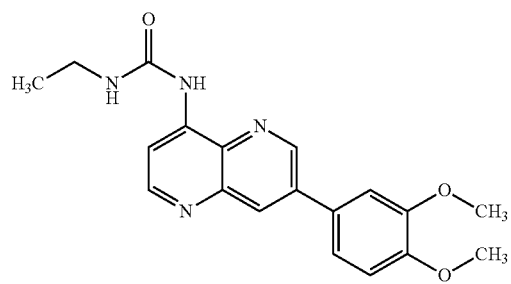 [SMILES: CCNC(=O)Nc1ccnc2cc(-c3ccc(OC)c(OC)c3)cnc12]

Under argon atmosphere, 100 mg (338 pmol, 1 eq) of 1-(7-bromo-[1,5]naphthyridin-4-yl)-3-ethyl-urea, 122 mg (676 μmol, 2 eq) of 3,4-dimethoxyphenylboronic acid, 108 mg (1.02 mmol, 3 eq) of sodium carbonate and 39 mg (34 μmol, 0.1 eq) of tetrakis(triphenylphosphine)palladium were introduced in 11 mL of a dimethylformamide/H₂O mixture (10/1). The mixture was stirred at 80° C. for 16 h. The mixture was allowed to reach rt and water was added. Aqueous layer was extracted with methylene chloride. Organic layers were dried over Na₂SO₄, filtered and evaporated to dryness. The residue was purified by column chromatography using methylene chloride/ethanol: 96/4 as eluent. The solvent was evaporated to dryness to afford, after trituration in diisopropyl ether, 80 mg of white powder with 67% yield.

Yield: 80 mg (67% of theory).

m.p.: 215-216° C.

¹H-NMR (DMSO-d₆, 400 MHz): δ=9.69 (s, 1H); 9.23 (d, 1H); 8.77 (d, 1H); 8.58 (d, 1H); 8.38 (d, 1H); 7.71 (t, 1H); 7.55-7.50 (m, 2H); 7.17 (d, 1H); 3.95 (s, 3H); 3.87 (s, 3H); 3.29-3.16 (m, 2H); 1.14 (t, 3H) ppm.

MS: m/z 353 (M+H⁺).

The examples below were synthesized analogously to Example 10.1: 1-[7-(3,4-Dimethoxy-phenyl)-[1,5]naphthyridin-4-yl]-3-ethyl-urea (7).

Example 10.2

1-tert-Butyl-3-[7-(3,4-dimethoxy-phenyl)-[1,5]naphthyridin-4-yl]-urea (8)

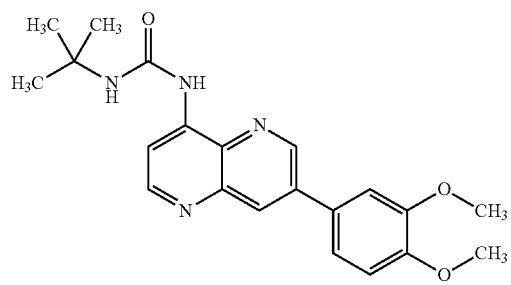 [SMILES: COc1ccc(-c2cnc3c(NC(=O)NC(C)(C)C)ccnc3c2)cc1OC]

Yield: 61 mg (52% of theory).

m.p.: 215-216° C.

¹H-NMR (DMSO-d₆, 400 MHz): δ=9.67 (s, 1H); 9.21 (d, 1H); 8.72 (d, 1H); 8.57 (d, 1H); 8.36 (d, 1H); 7.63 (s, 1H); 7.55-7.50 (m, 2H); 7.17 (d, 1H); 3.95 (s, 3H); 3.87 (s, 3H); 1.14 (s, 9H) ppm.

MS: m/z 381 (M+H⁺).

Example 10.3

1-Ethyl-3-[7-(4-hydroxy-3-methoxy-phenyl)-[1,5]naphthyridin-4-yl]-urea (9)

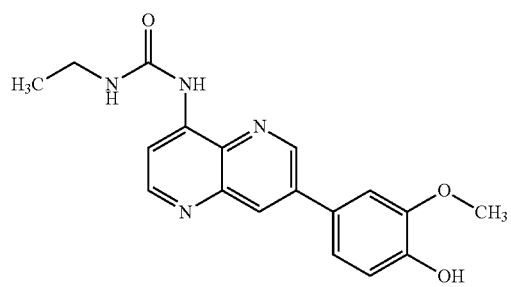 [SMILES: CCNC(=O)Nc1ccnc2cc(-c3ccc(O)c(OC)c3)cnc12]

Yield: 54 mg (47% of theory).

m.p.: 202-203° C.

¹H-NMR (DMSO-d₆, 400 MHz): δ=9.88 (s, 1H); 9.49 (s, 1H); 9.26 (d, 1H); 8.80 (d, 1H); 8.54 (d, 1H); 8.43 (d, 1H); 7.77 (t, 1H); 7.51 (s, 1H); 7.42 (d, 1H); 7.00 (d, 1H); 3.95 (s, 3H); 3.28-3.18 (m, 2H); 1.14 (t, 3H) ppm.

MS: m/z 339 (M+H⁺).

Example 10.4

1-Ethyl-3-[7-(1-methyl-1H-pyrazol-4-yl)-[1,5]naphthyridin-4-yl]-urea (10)

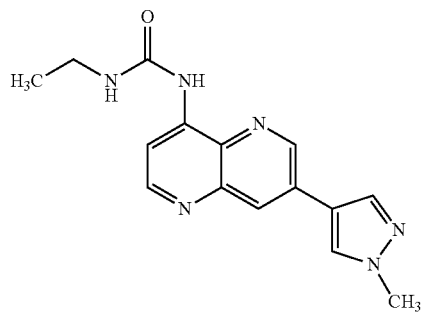 [SMILES: CCNC(=O)Nc1ccnc2cc(-c3cnn(C)c3)cnc12]

Yield: 51 mg (56% of theory).

m.p.: 215-216° C.

¹H-NMR (DMSO-d₆, 400 MHz): δ=9.64 (s, 1H); 9.18 (d, 1H); 8.71 (d, 1H); 8.56 (s, 1H); 8.49 (d, 1H); 8.32 (d, 1H); 8.26 (s, 1H); 7.68 (t, 1H); 3.96 (s, 3H); 3.23-3.19 (m, 2H); 1.14 (t, 3H) ppm.

MS: m/z 297 (M+H⁺).

Example 10.5

1-tert-Butyl-3-[7-(1-methyl-1H-pyrazol-4-yl)-[1,5]naphthyridin-4-yl]-urea (11)

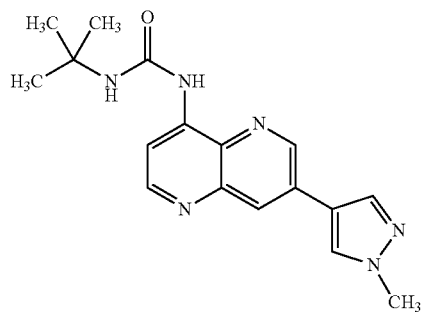 [SMILES: Cn1cc(-c2cnc3c(NC(=O)NC(C)(C)C)ccnc3c2)cn1]

Yield: 52 mg (52% of theory).

m.p.: 215-216° C.

¹H-NMR (DMSO-d₆, 400 MHz): δ=9.61 (s, 1H); 9.16 (d, 1H); 8.70 (d, 1H); 8.56 (s, 1H); 8.48 (d, 1H); 8.31 (d, 1H); 8.25 (s, 1H); 7.61 (s, 1H); 3.96 (s, 3H); 1.37 (s, 9H) ppm.

MS: m/z 325 (M+H⁺).

Example 10.6

1-tert-Butyl-3-[7-(4-hydroxy-3-methoxy-phenyl)-[1,5]naphthyridin-4-yl]-urea (12)

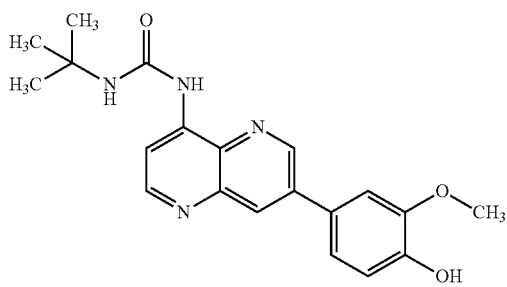 [SMILES: COc1cc(-c2cnc3c(NC(=O)NC(C)(C)C)ccnc3c2)ccc1O]

Yield: 100 mg (62% of theory).

m.p.: 158-159° C.

$^1$H-NMR (DMSO-d$_6$, 400 MHz): δ =9.66 (s, 1H); 9.41 (s, 1H); 9.19 (d, 1H); 8.73 (d, 1H); 8.53 (d, 1H); 8.35 (d, 1H); 7.62 (s, 1H); 7.50 (d, 1H); 7.40 (dd, 1H); 7.99 (d, 1H); 3.95 (s, 3H); 1.14 (s, 9H) ppm.

MS: m/z 367 (M+H$^+$).

Example 10.7

1-tert-Butyl-3-[7-(3,5-dichloro-4-hydroxy-phenyl)-[1,5]naphthyridin-4-yl]-urea (13)

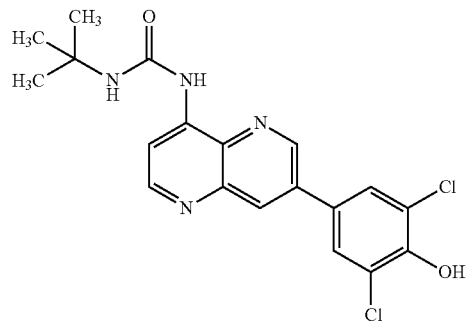 [SMILES: CC(C)(C)NC(=O)Nc1ccnc2cc(-c3cc(Cl)c(O)c(Cl)c3)cnc12]

Yield: 52 mg (41% of theory).

m.p.: >300° C.

$^1$H-NMR (DMSO-d$_6$, 400 MHz): δ =10.57 (s, 1H); 9.67 (s, 1H); 9.21 (d, 1H); 8.75 (d, 1H); 8.60 (d, 1H); 8.38 (d, 1H); 8.06 (s, 2H); 7.65 (s, 1H); 1.38 (t, 9H) ppm.

MS: m/z 405 (M+H$^+$); 407 ((M+2)+H$^+$); 409 ((M+4)+H$^+$).

Example 10.8

1-Cyclopropyl-3-[7-(4-hydroxy-3-methoxy-phenyl)-[1,5]naphthyridin-4-yl]-urea (14)

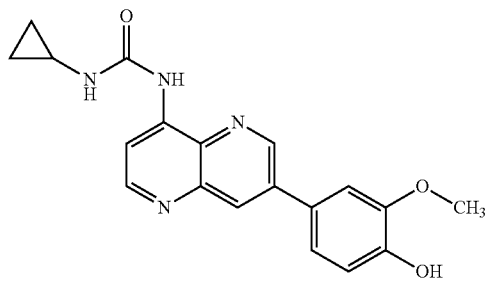 [SMILES: COc1cc(-c2cnc3c(NC(=O)NC4CC4)ccnc3c2)ccc1O]

Yield: 20 mg (17% of theory).

m.p.: 235-236° C.

$^1$H-NMR (DMSO-d$_6$, 400 MHz): δ =9.63 (s, 1H); 9.42 (s, 1H); 9.21 (s, 1H); 8.78 (d, 1H); 8.55 (s, 1H); 8.34 (d, 1H); 7.85 (s, 1H); 7.51 (s, 1H); 7.41 (d, 1H); 6.98 (d, 1H); 3.95 (s, 3H); 2.72-2.64 (m, 1H); 0.74 and 0.50 (bs, 4H) ppm.

MS: m/z 351 (M+H$^+$).

Example 10.9

1-[7-(3,5-Dichloro-4-hydroxy-phenyl)-[1,5]naphthyridin-4-yl]-3-ethyl-urea (15)

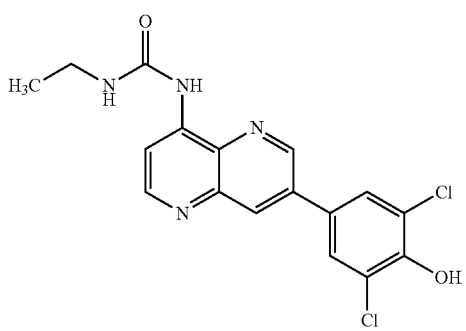 [SMILES: CCNC(=O)Nc1ccnc2cc(-c3cc(Cl)c(O)c(Cl)c3)cnc12]

Yield: 23 mg (20% of theory).

m.p.: >300° C.

$^1$H-NMR (DMSO-d$_6$, 400 MHz): δ =10.59 (s, 1H); 9.69 (s, 1H); 9.23 (d, 1H); 8.78 (d, 1H); 8.61 (d, 1H); 8.40 (d, 1H); 8.05 (s, 2H); 7.73 (t, 1H); 3.25-3.17 (m, 2H); 1.14 (t, 3H) ppm.

MS: m/z 377 (M+H$^+$); 379 ((M+2)+H$^+$); 381 ((M+4)+H$^+$).

Example 10.10

1-Ethyl-3-[7-(4-hydroxy-3,5-dimethyl-phenyl)-[1,5]naphthyridin-4-yl]-urea (16)

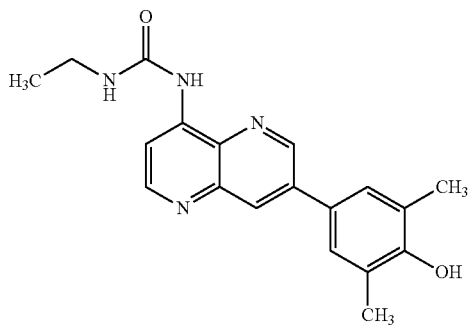 [SMILES: CCNC(=O)Nc1ccnc2cc(-c3cc(C)c(O)c(C)c3)cnc12]

Yield: 60 mg (52% of theory).
m.p.: 213-214° C.
$^1$H-NMR (DMSO-d$_6$, 400 MHz): δ=9.69 (s, 1H); 9.19 (d, 1H); 8.75 (d, 1H); 8.66 (s, 1H); 8.44 (d, 1H); 8.36 (d, 1H); 7.70 (t, 1H); 7.56 (s, 2H); 3.23-3.19 (m, 2H); 2.32 (s, 6H); 1.14 (t, 3H) ppm.
MS: m/z 337 (M+H$^+$).

Example 10.11

1-Cyclobutyl-3-[7-(1-methyl-1H-pyrazol-4-yl)-[1,5]naphthyridin-4-yl]-urea (17)

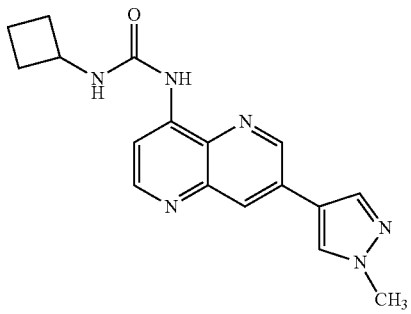 [SMILES: Cn1cc(-c2cnc3c(NC(=O)NC4CCC4)ccnc3c2)cn1]

Yield: 53 mg (53% of theory).
m.p.: 215-216° C.
$^1$H-NMR (DMSO-d$_6$, 400 MHz): δ=9.57 (s, 1H); 9.19 (d, 1H); 8.71 (d, 1H); 8.56 (s, 1H); 8.49 (d, 1H); 8.30 (d, 1H); 8.26 (s, 1H); 8.00 (d, 1H); 4.26-4.18 (m, 1H); 3.96 (s, 3H); 2.33-2.24 and 1.95-1.86 (m, 4H); 1.75-1.64 (m, 2H) ppm.
MS: m/z 323 (M+H$^+$).

Example 10.12

1-Cyclopropyl-3-[7-(1-methyl-1H-pyrazol-4-yl)-[1,5]naphthyridin-4-yl]-urea (18)

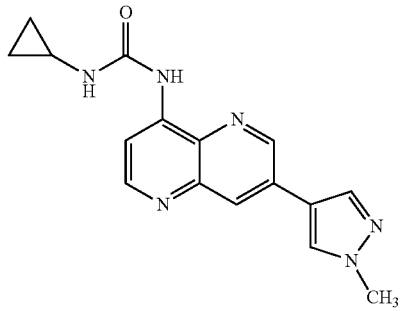 [SMILES: Cn1cc(-c2cnc3c(NC(=O)NC4CC4)ccnc3c2)cn1]

Yield: 53 mg (58% of theory).
m.p.: 223-224° C.
$^1$H-NMR (DMSO-d$_6$, 400 MHz): δ=9.59 (s, 1H); 9.18 (d, 1H); 8.74 (d, 1H); 8.56 (s, 1H); 8.50 (d, 1H); 8.32 (d, 1H); 8.25 (s, 1H); 7.83 (bs, 1H); 3.96 (s, 3H); 2.71-2.64 (m, 1H); 0.73 and 0.49 (bs, 4H) ppm.
MS: m/z 309 (M+H$^+$).

Example 10.13

1-[7-(1-Methyl-1H-pyrazol-4-yl)-[1,5]naphthyridin-4-yl]-3-propyl-urea (19)

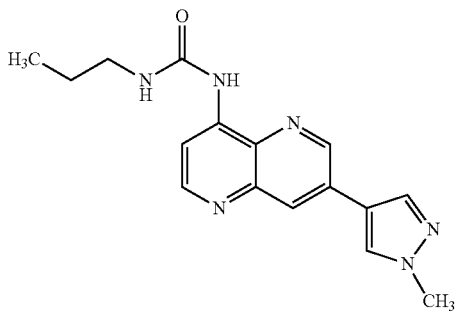 [SMILES: CCCNC(=O)Nc1ccnc2cc(-c3cnn(C)c3)cnc12]

Yield: 72 mg (70% of theory).
m.p.: 216-217° C.
$^1$H-NMR (DMSO-d$_6$, 400 MHz): δ=9.68 (s, 1H); 9.18 (s, 1H); 8.72 (d, 1H); 8.56 (s, 1H); 8.49 (s, 1H); 8.33 (d, 1H); 8.25 (s, 1H); 7.07 (bs, 1H); 3.96 (s, 3H); 3.15 (q, 2H); 1.56-1.49 (m, 2H); 0.96 (t, 3H) ppm.
MS: m/z 311 (M+H$^+$).

Example 10.14

1-[7-(1-Methyl-1H-pyrazol-4-yl)-[1,5]naphthyridin-4-yl]-3-(2,2,2-trifluoro-ethyl)-urea (20)

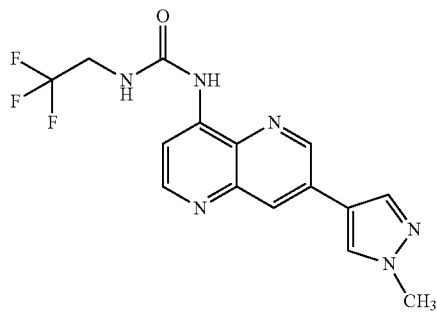 [SMILES: Cn1cc(-c2cnc3c(NC(=O)NCC(F)(F)F)ccnc3c2)cn1]

Yield: 71 mg (63% of theory).
m.p.: >300° C.
$^1$H-NMR (DMSO-d$_6$, 400 MHz): δ=9.95 (s, 1H); 9.22 (d, 1H); 8.76 (d, 1H); 8.57 (s, 1H); 8.52 (d, 1H); 8.33 (t, 1H); 8.32 (d, 1H); 8.27 (s, 1H); 4.13-4.02 (m, 2H); 3.96 (s, 3H) ppm.
MS: m/z 351 (M+H$^+$).

Example 10.15

1-[7-(1-Methyl-1H-pyrazol-4-yl)-[1,5]naphthyridin-4-yl]-3-(4-phenyl-butyl)-urea (21)

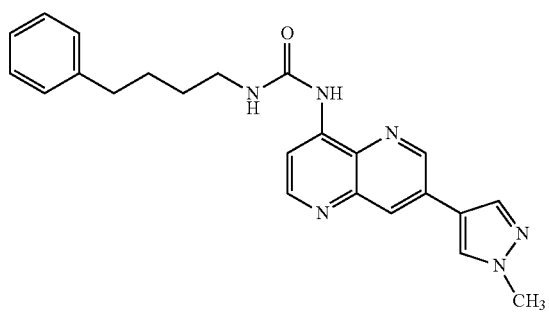 [SMILES: Cn1cc(-c2cnc3c(NC(=O)NCCCCc4ccccc4)ccnc3c2)cn1]

Yield: 70 mg (60% of theory).
m.p.: 185-186° C.
$^1$H-NMR (DMSO-d$_6$, 400 MHz): δ=9.66 (s, 1H); 9.18 (d, 1H); 8.72 (d, 1H); 8.56 (s, 1H); 8.49 (d, 1H); 8.32 (d, 1H); 8.26 (s, 1H); 7.69 (t, 1H); 7.34-7.19 (m, 5H); 3.96 (s, 3H); 3.22 (q, 2H); 2.65 (t, 2H); 1.72-1.64 (m, 2H); 1.56-1.49 (m, 2H) ppm.
MS: m/z 401 (M+H$^+$).

Example 10.16

1-Cyclohexyl-3-[7-(1-methyl-1H-pyrazol-4-4yl)-[1,5]naphthyridin-4-yl]-urea (22)

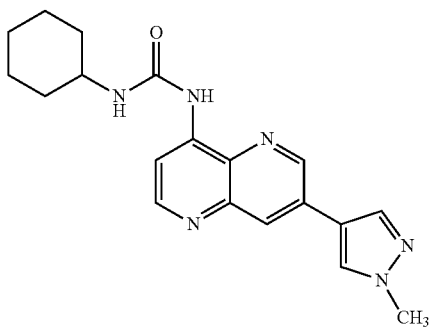 [SMILES: Cn1cc(-c2cnc3c(NC(=O)NC4CCCCC4)ccnc3c2)cn1]

Yield: 30 mg (30% of theory).
m.p.: 200-201° C.
$^1$H-NMR (DMSO-d$_6$, 400 MHz): δ=9.64 (s, 1H); 9.18 (d, 1H); 8.71 (d, 1H); 8.57 (s, 1H); 8.49 (d, 1H); 8.32 (d, 1H); 8.26 (s, 1H); 7,69 (d, 1H); 3.60-3.58 (m, 1H); 1.21-1.94 (m, 10H); 3.97 (s, 3H) ppm.
MS: m/z 351 (M+H$^+$).

Example 10.17

1-[7-(1-Methyl-1H-pyrazol-4-yl)-[1,5]naphthyridin-4-yl]-3-phenyl-urea (23)

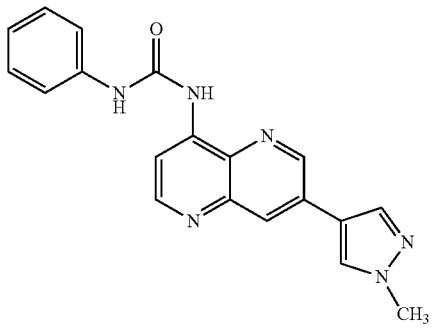 [SMILES: Cn1cc(-c2cnc3c(NC(=O)Nc4ccccc4)ccnc3c2)cn1]

Yield: 33 mg (33% of theory).
m.p.: 294-295° C.
$^1$H-NMR (DMSO-d$_6$, 400 MHz): δ=10.10 (s, 1H); 10.00 (s, 1H); 9.25 (d, 1H); 8.80 (d, 1H); 8.59 (s, 1H); 8.55 (d, 1H); 8.39 (d, 1H); 8.29 (s, 1H); 7.58 (d, 2H); 7.38 (dd, 2H); 7.08 (t, 1H); 3.99 (s, 3H) ppm.
MS: m/z 345 (M+H$^+$).

Example 10.18

1-(3,3-Difluoro-cyclobutyl)-3-[7-(1-methyl-1H-pyrazol-4-yl)-[1,5]naphthyridin-4-yl]-urea (24)

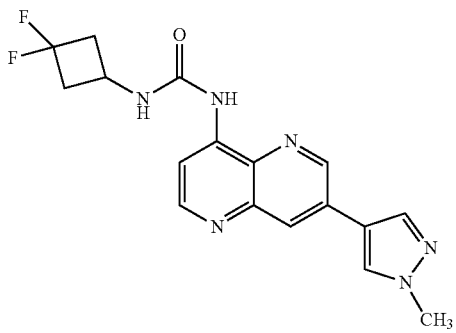 [SMILES: Cn1cc(-c2cnc3c(NC(=O)NC4CC(F)(F)C4)ccnc3c2)cn1]

Yield: 14 mg (14% of theory).
m.p.: 229-230° C.
$^1$H-NMR (DMSO-d$_6$, 400 MHz): δ=9.65 (s, 1H); 9.20 (d, 1H); 8.73 (d, 1H); 8.57 (s, 1H); 8.50 (d, 1H); 8.30 (d, 1H); 8.26 (s, 1H, H$_b$); 8.24 (d, 1H); 4.12 (s, 1H); 3.96 (s, 3H); 3.07-2.61 (m, 4H) ppm.
MS: m/z 359 (M+H$^+$).

Example 10.19

1-Hexyl-3-[7-(1-methyl-1H-pyrazol-4-yl)-[1,5]naphthyridin-4-yl]-urea (25)

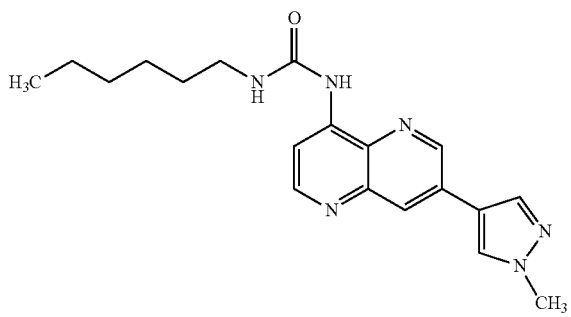 [SMILES: CCCCCCNC(=O)Nc1ccnc2cc(-c3cnn(C)c3)cnc12]

Yield: 50 mg (32% of theory).
m.p.: 188-189° C.
$^1$H-NMR (DMSO-d$_6$, 400 MHz): δ=9.67 (s, 1H); 9.18 (d, 1H); 8.71 (d, 1H); 8.56 (s, 1H); 8.49 (d, 1H); 8.32 (d, 1H); 8.25 (s, 1H); 7.68 (t, 1H); 3.96 (s, 3H); 3.18 (dt, 2H); 1.53-1.46 (m, 2H); 1.40-1.32 (m, 6H); 0.91 (t, 3H) ppm.
MS: m/z 352 (M+H$^+$).

Example 10.20

1-Isopropyl-3-[7-(1-methyl-1H-pyrazol-4-yl)-[1,5]naphthyridin-4-yl]-urea (30)

Yield: 25 mg (30% of theory)
m.p.: 259-230° C.
$^1$H-NMR (DMSO-d$_6$, 400 MHz): δ=9.58 (s, 1H); 9.18 (d, 1H); 8.71 (d, 1H); 8.56 (s, 1H); 8.49 (d, 1H); 8.32 (d, 1H); 8.25 (s, 1H); 7.65 (d, 1H); 3.96 (s, 3H); 3.88-3.83 (m, 1H); 1.71 (d, 6H) ppm.
MS: m/z 311 (M+H$^+$).

Example 10.21

1-Benzyl-3-[7-(1-methyl-1H-pyrazol-4-yl)-[1,5]naphthyridin-4-yl]-urea (31)

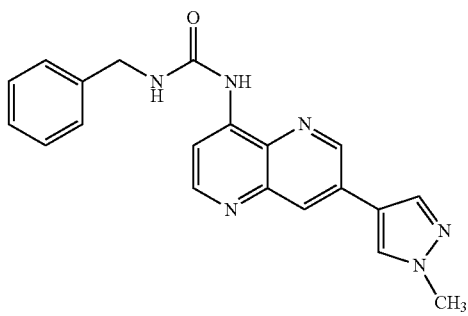 [SMILES: Cn1cc(-c2cnc3c(NC(=O)NCc4ccccc4)ccnc3c2)cn1]

Yield: 50 mg (38% of theory)
m.p.: 237-238° C.
$^1$H-NMR (DMSO-d$_6$, 400 MHz): δ=9.81 (s, 1H); 9.19 (d, 1H); 8.73 (d, 1H); 8.56 (s, 1H); 8.50 (d, 1H); 8.35 (d, 1H); 8.26 (s, 1H); 8.18 (t, 1H); 7.42-7.29 (m, 5H); 4.42 (d, 2H); 3.97 (s, 3H) ppm.
MS: m/z 359 (M+H$^+$).

Example 10.22

1-Butyl-3-[7-(1-methyl-1H-pyrazol-4-yl)-[1,5]naphthyridin-4-yl]-urea (32)

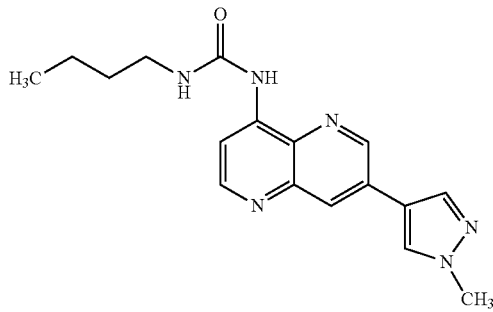 [SMILES: CCCCNC(=O)Nc1ccnc2cc(-c3cnn(C)c3)cnc12]

Yield: 14 mg (24% of theory)

m.p.: 219-220° C.

$^1$H-NMR (DMSO-d$_6$, 400 MHz): δ=10.12 (s, 1H); 8.86 (d, 1H); 8.64 (d, 1H); 8.48 (s, 1H); 8.38 (d, 1H); 7.97 (d, 1H); 7.87 (s, 1H); 7.60 (t, 1H); 3.95 (s, 3H); 3.42-3.40 (m, 2H); 1.68-1.65, 1.50-1.47 and 1.00-0.96 (m, 7H,) ppm.

MS: m/z 325 (M+H$^+$).

Example 10.23

1-[7-(1-Methyl-1H-pyrazol-4-yl)-[1,5]naphthyridin-4-yl]-3-phenethyl-urea (33)

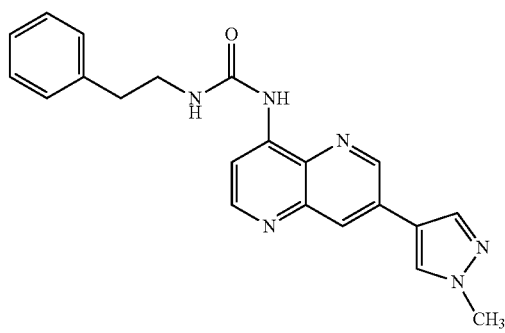 [SMILES: Cn1cc(-c2cnc3c(NC(=O)NCCc4ccccc4)ccnc3c2)cn1]

Yield: 50 mg (70% of theory)

m.p.: 222-223° C.

$^1$H-NMR (DMSO-d$_6$, 400 MHz): δ=9.71 (s, 1H); 9.17 (d, 1H); 8.72 (d, 1H); 8.56 (s, 1H); 8.49 (d, 1H); 8.34 (d, 1H); 8.25 (s, 1H); 7.75 (t, 1H); 7.38-7.24 (m, 5H); 3.96 (s, 3H); 3.48-3.43 (m, 2H); 2.84 (t, 2H) ppm.

MS: m/z 373 (M+H$^+$).

Example 10.24

1-Cyclopentyl-3-[7-(1-methyl-1H-pyrazol-4-yl)-[1,5]naphthyridin-4-yl]-urea (34)

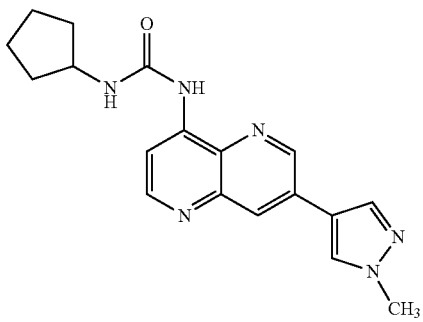 [SMILES: Cn1cc(-c2cnc3c(NC(=O)NC4CCCC4)ccnc3c2)cn1]

Yield: 14 mg (43% of theory)

m.p.: 207-208° C.

$^1$H-NMR (DMSO-d$_6$, 400 MHz): δ=9.60 (s, 1H); 9.18 (d, 1H); 8.71 (d, 1H); 8.56 (s, 1H); 8.48 (d, 1H); 8.32 (d, 1H); 8.26 (s, 1H); 7,75 (d, 1H); 4.10-4.02 (m, 1H); 3.97 (s, 3H); 1.92-1.26 (m, 8H) ppm.

MS: m/z 337 (M+H$^+$).

Example 10.25

1-Cyclopropyl-3-[7-(1H-pyrazol-4-yl)-[1,5]naphthyridin-4-yl]-urea (35)

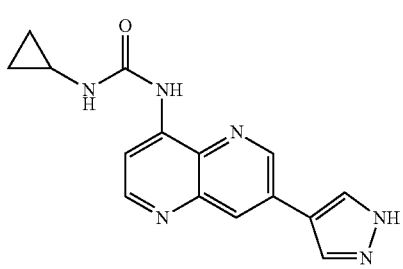 [SMILES: O=C(Nc1ccnc2cc(-c3cn[nH]c3)cnc12)NC1CC1]

Yield: 30 mg (13% of theory)

m.p.: 229-231° C.

$^1$H-NMR (DMSO-d$_6$, 600 MHz): δ=13.13 (s, 1H); 9.54 (s, 1H); 9.19 (s, 1H); 8.69 (d, 1H); 8.51 (s, 1H); 8.43 (s, 2H); 8.28 (d, 1H); 7.80 (s, 1H); 2.68-2.62 (m, 1H); 0.70 (s, 2H); 0.46 (s,2H) ppm.

MS: m/z 295 (M+H$^+$).

Example 10.26

1-Cyclopropyl-3-(7-thiophen-3-yl-[1,5]naphthyridin-4-yl)-urea (36)

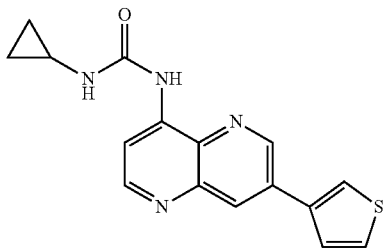 [SMILES: O=C(Nc1ccnc2cc(-c3ccsc3)cnc12)NC1CC1]

Yield: 159 mg (62% of theory)

m.p.: 228-229° C.

$^1$H-NMR (DMSO-d$_6$, 600 MHz): δ =9.58 (s, 1H); 9.29 (s, 1H); 8.74 (d, 1H); 8.62 (s, 1H); 8.35 (s, 1H); 8.33 (d, 1H); 7.88 (d, 1H); 7.81 (s, 1H); 7.77 (dd, 1H); 2.68-2.60 (m, 1H); 0.70 (s,2H); 0.46 (s,2H)ppm.

MS: m/z 311 (M+H$^+$).

Example 10.27

1-Cyclopropyl-3-[7-(2-fluoro-pyridin-4-yl)-[1,5]naphthyridin-4-yl]-urea (37)

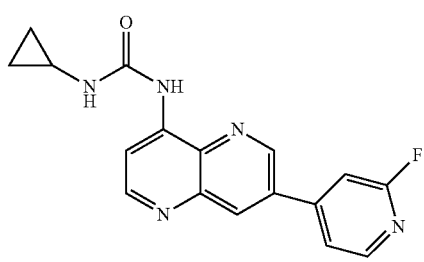 [SMILES: O=C(Nc1ccnc2cc(-c3ccnc(F)c3)cnc12)NC1CC1]

Yield: 68 mg (22% of theory)

m.p.: 226-229° C.

$^1$H-NMR (DMSO-d$_6$, 600 MHz): δ =9.65 (s, 1H); 9.32 (s, 1H); 8.82 (dd, 2H); 8.42 (d, 2H); 8.01 (d, 1H); 7.89 (s, 1H); 7.84 (s, 1H); 2.68-2.62 (m, 1H); 0.70 (s, 2H); 0.46 (s, 2H) ppm.

MS: m/z 324 (M+H$^+$).

Example 10.28

1-Cyclopropyl-3-{7-[1-(2-morpholin-4-yl-ethyl)-1H-pyrazol-4-yl]-[1,5]naphthyridin-4-yl}-urea (38)

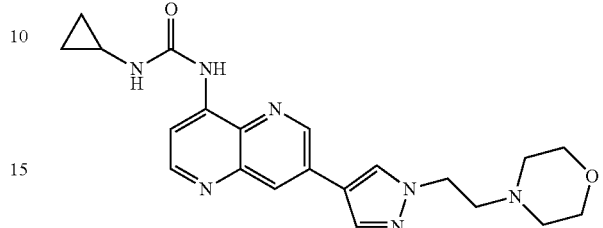

Yield: 280 mg (79% of theory)

m.p.: 127-129° C.

$^1$H-NMR (DMSO-d$_6$, 600 MHz): δ =9.54 (s, 1H); 9.14 (s, 1H); 8.70 (d, 1H); 8.56 (s, 1H); 8.46 (d, 1H); 8.29 (d, 1H); 8.22 (s, 1H); 7.80 (s, 1H); 4.30 (t, 2H); 3.60-3.54 (m, 4H); 2.78 (t, 2H); 2.67-2.60 (m, 1H); 2.47-2.41 (m, 4H); 0.70 (s, 2H); 0.46 (s, 2H) ppm.

MS: m/z 408 (M+H$^+$).

Example 10.29

1-Cyclopropyl-3-(7-phenyl-[1,5]naphthyridin-4-yl)-urea (39)

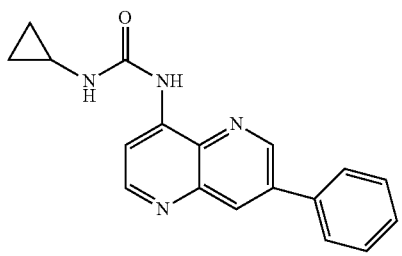 [SMILES: O=C(Nc1ccnc2cc(-c3ccccc3)cnc12)NC1CC1]

Yield: 80 mg (18% of theory)

m.p.: 188-190° C.

$^1$H-NMR (DMSO-d$_6$, 600 MHz): δ =9.63 (s, 1H); 9.21 (s, 1H); 8.77 (d, 1H); 8.56 (s, 1H); 8.37 (d, 1H); 7.94 (d, 2H); 7.81 (s, 1H); 7.58 (t, 2H); 7.50 (t, 1H); 2.68-2.62 (m, 1H); 0.70 (s, 2H); 0.46 (s, 2H);ppm.

MS: m/z 305 (M+H$^+$).

Example 10.30

1-Cyclopropyl-3-[7-(1H-indol-5-yl)-[1,5]naphthyridin-4-yl]-urea (40)

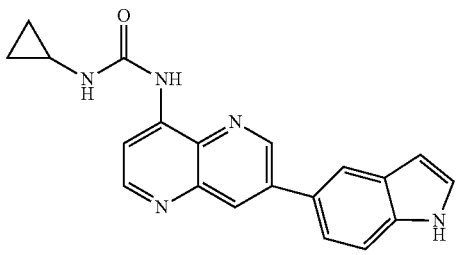 [SMILES: O=C(Nc1ccnc2cc(-c3ccc4[nH]ccc4c3)cnc12)NC1CC1]

Yield: 100 mg (22% of theory)
m.p.: 214-215° C.
$^1$H-NMR (DMSO-d$_6$, 600 MHz): δ =11.27 (s, 1H); 9.62 (s, 1H); 9.25 (s, 1H); 8.74 (d, 1H); 8.49 (s, 1H); 8.33 (d, 1H); 8.12 (s, 1H); 7.81 (s, 1H); 7.64 (d, 1H); 7.57 (d, 1H); 7.44 (t, 1H); 6.56 (s, 1H); 2.68-2.62 (m, 1H); 0.70 (s, 2H); 0.46 (s, 2H) ppm.
MS: m/z 344 (M+H$^+$).

Biological Actions of the Compounds According to the Invention

Cell-Free Kinase Assays (by ALPHA Technology)

The inhibitory effect of the inventive compounds was tested on various human serine/threonine kinases and tyrosine kinases in enzymatic assays. Recombinant human kinases, for example Aurora-B, cRaf-Mek1-Erk2, Erk2, Pim-1, HIPK1, KDR, TrkA, Yes, c-Abl and others were used, in some cases as full-length kinases, in some cases as truncated fragments—but at least consisting of the functional kinase domains. The commercial kinase proteins (Proqinase, Millipore) were used as recombinant fusion proteins with GST (glutathione S-transferase) tag or His tag. Depending on the substrate type, the different kinase reactions were quantified by suitable ALPHA™ beads (PerkinElmer).
Testing The kinase assay for Aurora-B is described in detail and selected test results are cited below. To determine the IC$_{50}$ value, the potential inhibitor substances were investigated at 10 half-logarithmically graduated concentrations of 3.16 nM-100 μM.

Aurora-B assay: The test substance, 1.25 ng of Aurora-B (#14-835, Upstate/Millipore), 10 μM ATP and 15 nM biotinylated PLK (#1300, Cell Signaling) substrate were incubated on a 384-well Optiplate (Perkin Elmer) in a volume of 15 μl for 1 h in 25 mM Tris, 10 mM MgCl$_2$, 0.1% Tween-20, 100 μM NaVO$_4$, 2 mM DTT at pH 7.5. The kinase reaction was stopped by adding 10 μl of the ALPHA bead mix (10 μg/ml, #6760617/PerkinElmer), pre-incubated with anti-phospho PLK antibody (100 pM, #5070, Cell Signaling), in 25 mM Tris, 200 mM NaCl, 100 mM EDTA and 0.3% BSA, and left to stand overnight.

The luminescence was detected the next morning in a Envision instrument (Perkin Elmer).
Evaluation The calculation of % inhibition values per substance concentration was done by means of the following formula from the raw data determined in the Envision reader:

$$\text{\% kinase inhibition}_{(sample)} = 100 - \left(100 \times \frac{\text{mean}_{(sample)} - \text{mean}_{(0\% \, control)}}{\text{mean}_{(100\% \, control)} - \text{mean}_{(0\% \, control)}}\right)$$

The controls were determined 16 fold. 0% controls contained no ATP whereas the 100% controls contained no test substance. The IC$_{50}$ values were determined with GraphPad-Prism.

The inventive compounds exhibited effective inhibition of Aurora-B and partly against Erk2 (see table 1).

TABLE 1

| Kinase assay test results (IC50 [μM] at 10 μM ATP) | | | |
|---|---|---|---|
| example | Aurora-B | cRaf-Mek-Erk | Erk2 |
| 1 | 2.23 | 1.55 | 1.13 |
| 2 | 0.624 | 0.621 | 0.742 |
| 3 | 0.805 | 1.12 | 1.72 |
| 4 | 0.227 | 0.339 | 0.702 |
| 5 | 0.171 | 0.008 | 0.733 |
| 7 | 0.136 | ca. 100 | >100 |
| 8 | 0.714 | ca. 100 | >100 |
| 9 | 0.370 | >31.6 | ca. 100 |
| 10 | 0.038 | >31.6 | >100 |
| 11 | 0.112 | 12.6 | >31.6 |
| 12 | 1.58 | >31.6 | >100 |
| 13 | 0.500 | 11.0 | >100 |
| 14 | 0.108 | 18.1 | >100 |
| 15 | 0.227 | 7.85 | >31.6 |
| 16 | 3.85 | >31.6 | >31.6 |
| 17 | 0.048 | 2.17 | >100 |
| 18 | 0.013 | 7.45 | >100 |
| 19 | 0.026 | 9.74 | >100 |
| 20 | 0.129 | 27.3 | >100 |
| 21 | 0.141 | 16.9 | >31.6 |
| 22 | 0.354 | >31.6 | >100 |
| 23 | 1.257 | >100 | >100 |
| 24 | 0.784 | 26.190 | >100 |
| 25 | 0.885 | >100 | >100 |
| 26 | 0.260 | 0.096 | 0.429 |
| 27 | 1.139 | 0.157 | 0.191 |
| 28 | 0.579 | 0.005 | 0.003 |
| 30 | 0.137 | 2.170 | >100 |
| 31 | 0.066 | >100 | >100 |
| 32 | 0.164 | 12.770 | >31.6 |
| 33 | 0.086 | 16.630 | >100 |
| 34 | 0.108 | 0.676 | 4.079 |
| 35 | 0.085 | 4.654 | >100 |
| 36 | 0.103 | 3.847 | >100 |
| 37 | 0.935 | 10.260 | >100 |
| 38 | 0.028 | 2.812 | >100 |
| 39 | 0.889 | 20.320 | >100 |
| 40 | 2.12 | >100 | >100 |

Especially Compounds 10, 17, 18, 19 and 38 are characterized by IC50 values under 100 nM against Aurora-B and show high selectivity against the other kinases.

Compounds 1, 2, 3, 4, 5, 26, 27, and 28 show dual activity against Aurora-B and Erk2 (or cRaf-Mek-Erk cascade respectively).

The invention claimed is:
1. A naphthyridine derivative of the general formula I

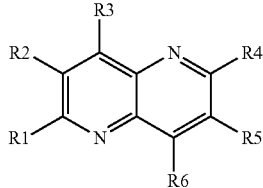

Formula I wherein
R1 and R3 are independently hydrogen or NR7R8, wherein at least one of R1 and R3 is NR7R8 wherein R7 is hydrogen, R8 is —C(Y)NR9R10, Y is O or S, R9 is hydrogen and R10 can independently be
(i) unsubstituted or substituted alkyl,
(ii) unsubstituted or substituted cycloalkyl,
(iii) unsubstituted or substituted heterocyclyl,
(iv) unsubstituted or substituted aryl,
(v) unsubstituted or substituted heteroaryl,
R2 is
(vi) hydrogen,
(vii) unsubstituted or substituted alkyl,
(viii) unsubstituted or substituted heterocyclyl,
(ix) unsubstituted or substituted aryl,
(x) unsubstituted or substituted heteroaryl,
(xi) halogen,
(xii) cyano,
(xiii) hydroxyl,
(xiv) alkoxy,
(xv) amino,
(xvi) carboxyl, alkoxycarbonyl, carboxyalkyl or alkoxycarbonylalkyl,
(xvii) alkoxycarbonylamino, alkoxycarbonylaminoalkyl, and
(xviii) NR7R8, wherein in R2 or R3 R7 is hydrogen, alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl may be optionally substituted, and R8 is —C(Y)NR9R10, where Y is O or S and R9 and R10 are independently of one another
(i) hydrogen,
(ii) unsubstituted or substituted alkyl,
(iii) unsubstituted or substituted cycloalkyl,
(iv) unsubstituted or substituted heterocyclyl,
(v) unsubstituted or substituted aryl,
(vi) unsubstituted or substituted heteroaryl,
(vii) or R9 and R10 together may be heterocyclyl, —C(Y)NR11R12, where Y is NH and R11 and R12 are independently of one another
(i) hydrogen,
(ii) unsubstituted or substituted alkyl,
(iii) unsubstituted or substituted cycloalkyl,
(iv) unsubstituted or substituted heterocyclyl,
(v) unsubstituted or substituted aryl,
(vi) unsubstituted or substituted heteroaryl,
(vii) or R11 and R12 together may be heterocyclyl, —C(NR13)R14 where R13 is H and R14 is
(i) unsubstituted or substituted alkyl,
(ii) unsubstituted or substituted cycloalkyl,
(iii) unsubstituted or substituted heterocyclyl,
(iv) unsubstituted or substituted aryl,
(v) unsubstituted or substituted heteroaryl,
R5 is a unsubstituted or substituted heteroaryl,
R4 and R6 are independently of one another:
(i) hydrogen,
(ii) unsubstituted or substituted alkyl,
(iii) unsubstituted or substituted cycloalkyl,
(iv) unsubstituted or substituted heterocyclyl,
(v) unsubstituted or substituted aryl,
(vi) unsubstituted or substituted heteroaryl,
(vii) halogen,
(viii) cyano,
(ix) hydroxyl,
(x) alkoxy,
(xi) NR15R16, where R15 and R16 are, independently of each other, hydrogen, alkyl, cycloalkyl, heterocyclyl, aryl, heteroaryl, alkylcyclyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl are optionally substituted,
or R15 and R16 are together heterocyclyl, where heterocyclyl is optionally substituted,
(xii) OR17, where R17 can be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl, heteroaryl, alkylcycloalkyl, alkylheterocyclyl, alkylaryl or alkylheteroaryl are optionally substituted,
(xiii) SR18, where R18 can be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl are optionally substituted,
their physiologically acceptable salts, hydrates, solvates, where the compounds of the general formula (I) and their salts, hydrates or solvates may be present in the form of their racemates, enantiomers and/or diastereomers, or in the form of mixtures of the enantiomers and/or diastereomers, in the form of the tautomers and their polymorphic forms.
2. The naphthyridine derivative of the general formula I according to claim 1 in which
R2 is
(i) hydrogen,
(ii) unsubstituted or substituted alkyl,
(iii) unsubstituted or substituted heterocyclyl,
(iv) unsubstituted or substituted aryl,
(v) unsubstituted or substituted heteroaryl,
(vi) halogen,
(vii) cyano,
(viii) hydroxyl,
(ix) alkoxy,
(x) amino,
(xi) carboxyl, alkoxycarbonyl, carboxyalkyl or alkoxycarbonylalkyl,
(xii) alkoxycarbonylamino, alkoxycarbonylaminoalkyl, and
R4 and R6 are independently of one another:
(i) hydrogen,
(ii) unsubstituted or substituted alkyl,
(iii) unsubstituted or substituted cycloalkyl,
(iv) unsubstituted or substituted heterocyclyl,
(v) unsubstituted or substituted aryl,
(vi) unsubstituted or substituted heteroaryl,
(vii) halogen, (viii) cyano,
(ix) hydroxyl,
(x) alkoxy,
(xi) NR15R16, where R15 and R16 are, independently of each other, hydrogen, alkyl, cycloalkyl, heterocyclyl, aryl, heteroaryl, alkylcyclyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl are optionally substituted,
or R15 and R16 are together heterocyclyl, where heterocyclyl is optionally subtituted,
(xii) OR17, where R17 can be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl, heteroaryl, alkylcycloalkyl, alkylheterocyclyl, alkylaryl or alkylheteroaryl are optionally susbtituted,
(xiii) SR18, where R18 can be alkyl, cycloalkyl, heterocyclyl, aryl, heteroaryl, alkylcycloalkyl, alkylheterocyclyl, alkylaryl or alkylheteroaryl, and the alkyl, cycloalkyl, heterocyclyl, aryl and heteroaryl, alkylcycloalkyl, alkylheterocyclyl, alkylaryl or alkylheteroaryl are optionally susbtituted.

3. The naphthyridine derivative of the general formula I according to claim 1 in which
R2 is
(i) hydrogen,
(ii) unsubstituted or substituted alkyl,
R4 and R6 are independently of one another:
(i) hydrogen,
(ii) unsubstituted or substituted alkyl.

4. The naphthyridine derivative of the general formula I according to claim 1, selected from the group consisting of:

| # | Structure | Name |
|---|-----------|------|
| 5 | 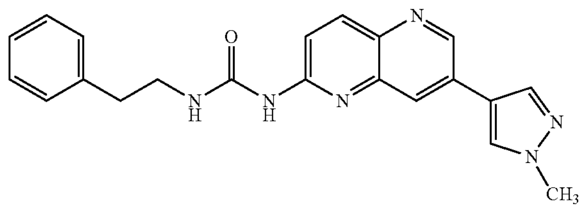 [SMILES: Cn1cc(-c2cnc3ccc(NC(=O)NCCc4ccccc4)nc3c2)cn1] | 1-[7-(1-Methyl-1H-pyrazol-4-yl)-[1,5]naphthyridin-2-yl]-3-phenethyl-urea |
| 10 | 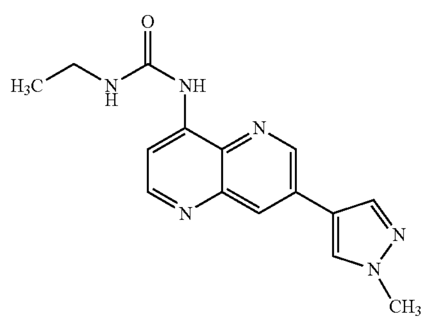 [SMILES: CCNC(=O)Nc1ccnc2cc(-c3cnn(C)c3)cnc12] | 1-Ethyl-3-[7-(1-methyl-1H-pyrazol-4-yl)-[1,5]naphthyridin-4-yl]-urea |
| 11 | 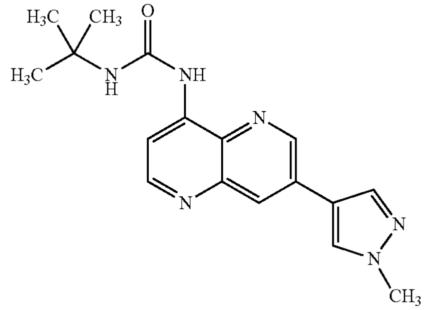 [SMILES: Cn1cc(-c2cnc3c(NC(=O)NC(C)(C)C)ccnc3c2)cn1] | 1-tert-Butyl-3-[7-(1-methyl-1H-pyrazol-4-yl)-[1,5]naphthyridin-4-yl]-urea |

-continued

| # | Structure | Name |
|---|---|---|
| 17 | 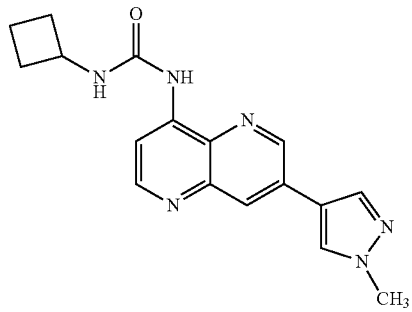 [SMILES: Cn1cc(-c2cnc3c(NC(=O)NC4CCC4)ccnc3c2)cn1] | 1-Cyclobutyl-3-[7-(1-methyl-1H-pyrazol-4-yl)-[1,5]naphthyridin-4-yl]-urea |
| 18 | 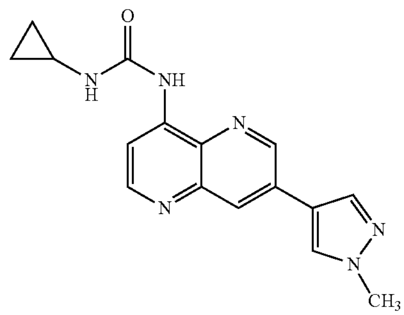 [SMILES: Cn1cc(-c2cnc3c(NC(=O)NC4CC4)ccnc3c2)cn1] | 1-Cyclopropyl-3-[7-(1-methyl-1H-pyrazol-4-yl)-[1,5]naphthyridin-4-yl]-urea |
| 19 | 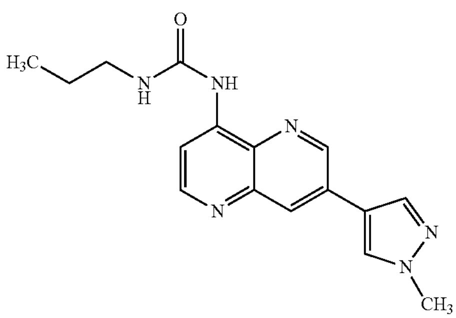 [SMILES: CCCNC(=O)Nc1ccnc2cc(-c3cnn(C)c3)cnc12] | 1-[7-(1-Methyl-1H-pyrazol-4-yl)-[1,5]naphthyridin-4-yl]-3-propyl-urea |
| 20 | 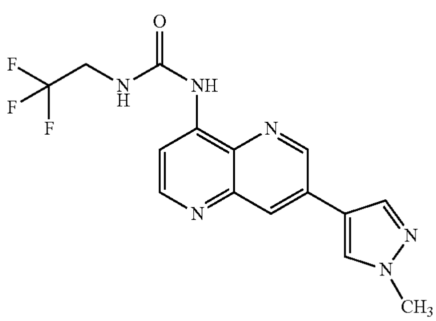 [SMILES: Cn1cc(-c2cnc3c(NC(=O)NCC(F)(F)F)ccnc3c2)cn1] | 1-[7-(1-Methyl-1H-pyrazol-4-yl)-[1,5]naphthyridin-4-yl]-3-(2,2,2-trifluoro-ethyl)-urea |
| 21 | 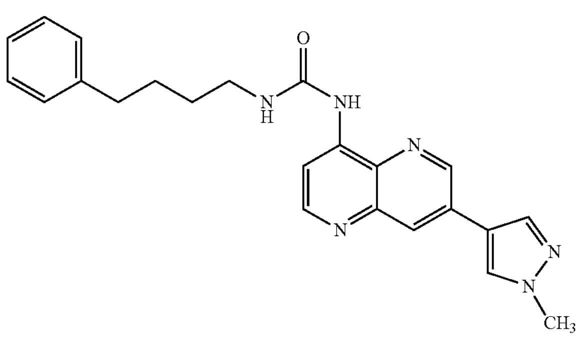 [SMILES: Cn1cc(-c2cnc3c(NC(=O)NCCCCc4ccccc4)ccnc3c2)cn1] | 1-[7-(1-Methyl-1H-pyrazol-4-yl)-[1,5]naphthyridin-4-yl]-3-(4-phenyl-butyl)-urea |

-continued

| # | Structure | Name |
|---|---|---|
| 22 | 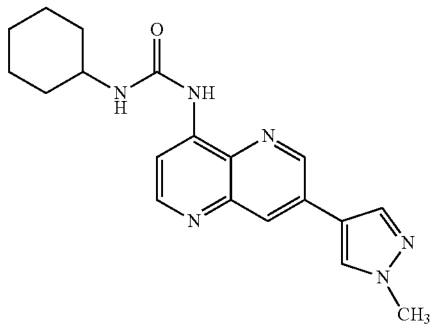 [SMILES: Cn1cc(-c2cnc3c(NC(=O)NC4CCCCC4)ccnc3c2)cn1] | 1-Cyclohexyl-3-[7-(1-methyl-1H-pyrazol-4-yl)-[1,5]naphthyridin-4-yl]-urea |
| 23 | 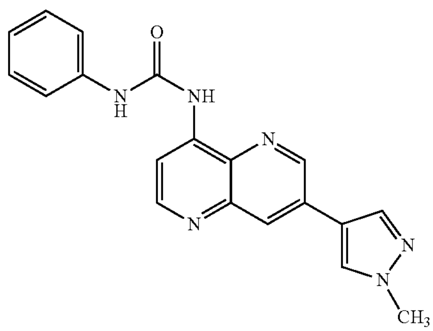 [SMILES: Cn1cc(-c2cnc3c(NC(=O)Nc4ccccc4)ccnc3c2)cn1] | 1-[7-(1-Methyl-1H-pyrazol-4-yl)-[1,5]naphthyridin-4-yl]-3-phenyl-urea |
| 24 | 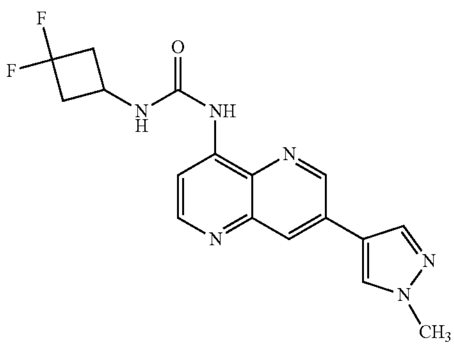 [SMILES: Cn1cc(-c2cnc3c(NC(=O)NC4CC(F)(F)C4)ccnc3c2)cn1] | 1-(3,3-Difluoro-cyclobutyl)-3-[7-(1-methyl-1H-pyrazol-4-yl)-[1,5]naphthyridin-4-yl]-urea |
| 25 | 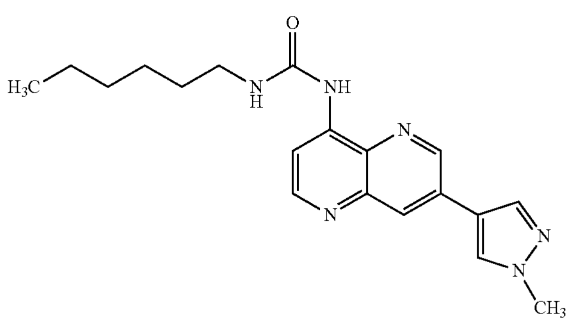 [SMILES: CCCCCCNC(=O)Nc1ccnc2cc(-c3cnn(C)c3)cnc12] | 1-Hexyl-3-[7-(1-methyl-1H-pyrazol-4-yl)-[1,5]naphthyridin-4-yl]-urea |
| 26 | 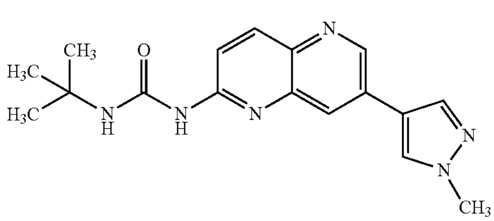 [SMILES: Cn1cc(-c2cnc3ccc(NC(=O)NC(C)(C)C)nc3c2)cn1] | 1-tert-Butyl-3-[7-(1-methyl-1H-pyrazol-4-yl)-[1,5]naphthyridin-2-yl]-urea |

-continued

| # | Structure | Name |
|---|---|---|
| 27 | 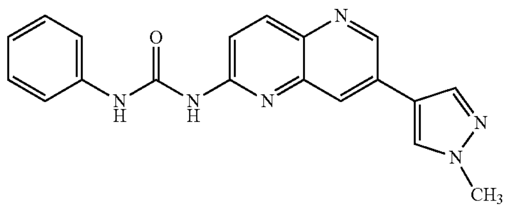 [SMILES: Cn1cc(-c2cnc3ccc(NC(=O)Nc4ccccc4)nc3c2)cn1] | 1-[7-(1-Methyl-1H-pyrazol-4-yl)-[1,5]naphthyridin-2-yl]-3-phenyl-urea |
| 28 | 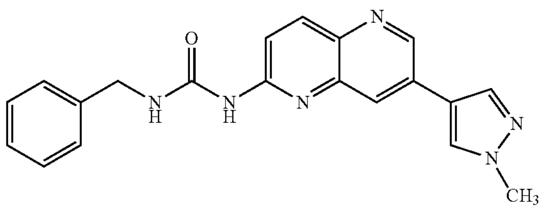 [SMILES: Cn1cc(-c2cnc3ccc(NC(=O)NCc4ccccc4)nc3c2)cn1] | 1-Benzyl-3-[7-(1-methyl-1H-pyrazol-4-yl)-[1,5]naphthyridin-2-yl]-urea |
| 29 | 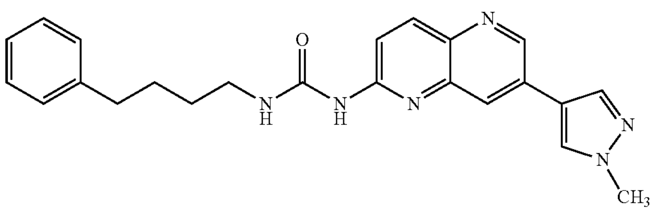 [SMILES: Cn1cc(-c2cnc3ccc(NC(=O)NCCCCc4ccccc4)nc3c2)cn1] | 1-[7-(1-Methyl-1H-pyrazol-4-yl)-[1,5]naphthyridin-2-yl]-3-(4-phenyl-butyl)-urea |
| 30 | 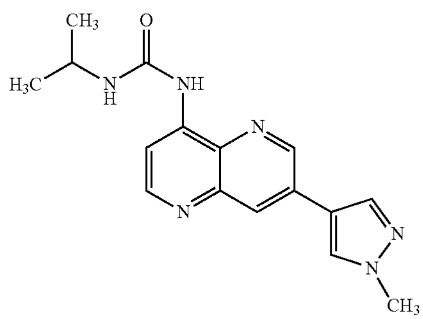 [SMILES: CC(C)NC(=O)Nc1ccnc2cc(-c3cnn(C)c3)cnc12] | 1-Isopropyl-3-[7-(1-methyl-1H-pyrazol-4-yl)-[1,5]naphthyridin-4-yl]-urea |
| 31 | 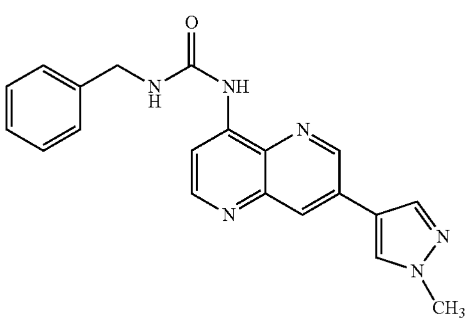 [SMILES: Cn1cc(-c2cnc3c(NC(=O)NCc4ccccc4)ccnc3c2)cn1] | 1-Benzyl-3-[7-(1-methyl-1H-pyrazol-4-yl)-[1,5]naphthyridin-4-yl]-urea |
| 32 | 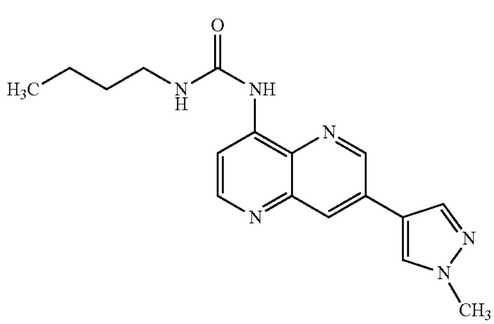 [SMILES: CCCCNC(=O)Nc1ccnc2cc(-c3cnn(C)c3)cnc12] | 1-Butyl-3-[7-(1-methyl-1H-pyrazol-4-yl)-[1,5]naphthyridin-4-yl]-urea |

| # | Structure | Name |
|---|---|---|
| 33 | 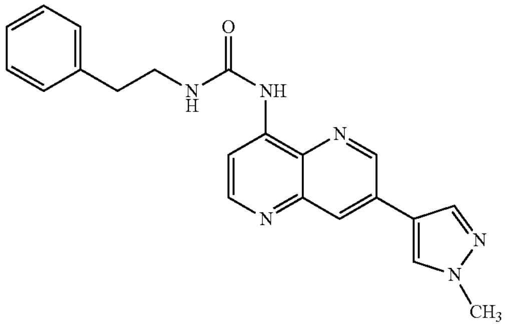 [SMILES: Cn1cc(-c2cnc3c(NC(=O)NCCc4ccccc4)ccnc3c2)cn1] | 1-[7-(1-Methyl-1H-pyrazol-4-yl)-[1,5]naphthyridin-4-yl]-3-phenethyl-urea |
| 34 | 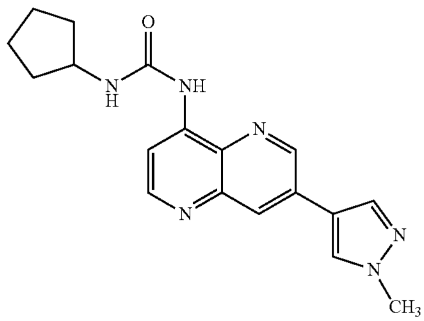 [SMILES: Cn1cc(-c2cnc3c(NC(=O)NC4CCCC4)ccnc3c2)cn1] | 1-Cyclopentyl-3-[7-(1-methyl-1H-pyrazol-4-yl)-[1,5]naphthyridin-4-yl]-urea |
| 35 | 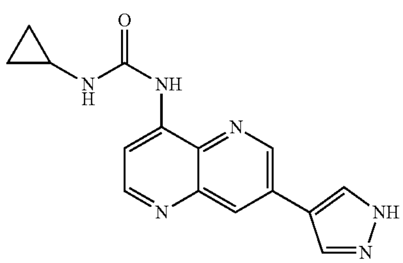 [SMILES: O=C(Nc1ccnc2cc(-c3cn[nH]c3)cnc12)NC1CC1] | 1-Cyclopropyl-3-[7-(1H-pyrazol-4-yl)-[1,5]naphthyridin-4-yl]-urea |
| 36 | 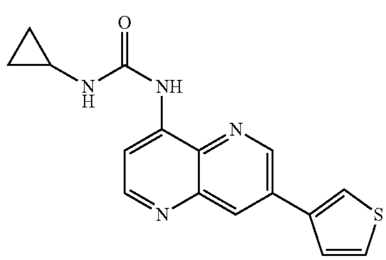 [SMILES: O=C(Nc1ccnc2cc(-c3ccsc3)cnc12)NC1CC1] | 1-Cyclopropyl-3-(7-thiophen-3-yl-[1,5]naphthyridin-4-yl)-urea |
| 37 | 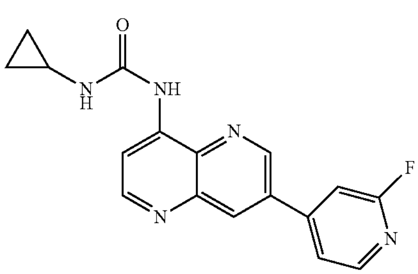 [SMILES: O=C(Nc1ccnc2cc(-c3ccnc(F)c3)cnc12)NC1CC1] | 1-Cyclopropyl-3-[7-(2-fluoro-pyridin-4-yl)-[1,5]naphthyridin-4-yl]-urea |

| # | Structure | Name |
|---|---|---|
| 38 | 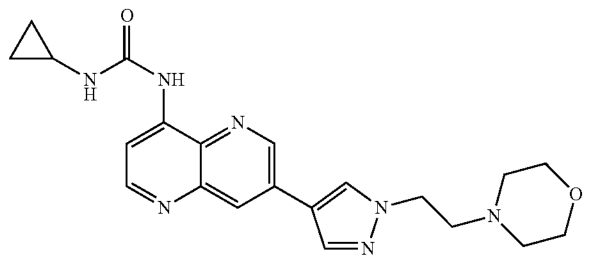 [SMILES: O=C(Nc1ccnc2cc(-c3cnn(CCN4CCOCC4)c3)cnc12)NC1CC1] | 1-Cyclopropyl-3-{7-[1-(2-morpholin-4-yl-ethyl)-1H-pyrazol-4-yl]-[1,5]naphthyridin-4-yl}-urea |
| 40 | 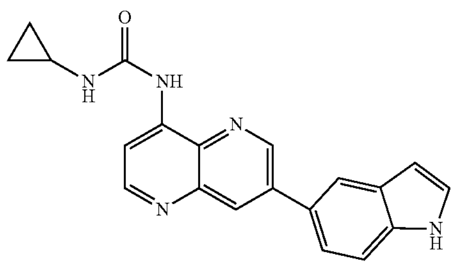 [SMILES: O=C(Nc1ccnc2cc(-c3ccc4[nH]ccc4c3)cnc12)NC1CC1] | 1-Cyclopropyl-3-[7-(1H-indol-5-yl)-[1,5]naphthyridin-4-yl]-urea. |

5. A pharmaceutical composition comprising a pharmacologically active amount of at least one compound according to claim 1.

6. The pharmaceutical composition according to claim 5 further comprising at least one further pharmacologically active substance.

7. The pharmaceutical composition according to claim 5 further comprising a pharmaceutically acceptable carrier and/or auxiliary.

8. The pharmaceutical composition according to claim 7 wherein the additional pharmacologically active substance is selected from the group consisting of:
asparaginase, bleomycin, carboplatin, carmustine, chlorambucil, cisplatin, colaspase, cyclophosphamide, cytarabine, dacarbazine, dactinomycin, daunorubicin, doxorubicin adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thalidomide, thioguanine, topotecan, vinblastine, vincristine, vindesine, aminoglutethimide, L-asparaginase, azathioprine, 5-azacytidine cladribine, busulphan, diethylstilbestrol, 2',2'-difluorodeoxycytidine, docetaxel, erythrohydroxynonyladenine, ethynylestradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbine, epothilone, gemcitabine, taxotere, BCNU, CCNU, DTIC, herceptin, avastin, erbitux, sorafenib (nexavar), imatinib (gleevec, glivec), gefitinib (iressa), erlotinib (tarceva), rapamycin, actinomycin D, sunitinib (sutent), dasatinib (sprycel), nilotinib (tasigna), lapatinib (tykerb, tyverb), vatalanib.

9. A process for preparing a medicament, comprising processing one or more naphthyridine derivatives according to claim 1 to a pharmaceutical preparation or converting the naphthyridine derivatives into a therapeutically usable form with pharmaceutically acceptable carriers and/or auxiliaries.

\* \* \* \* \*